(12) United States Patent
McEvoy et al.

(10) Patent No.: US 9,765,397 B2
(45) Date of Patent: Sep. 19, 2017

(54) METHOD OF DETECTING METHYLATION

(71) Applicant: CLINICAL GENOMICS PTY LTD, North Ryde (AU)

(72) Inventors: Aidan McEvoy, Manly (AU); Susanne Pedersen, North Ryde (AU); Rohan Baker, Avalon Beach (AU)

(73) Assignee: Clinical Genomics Pty Ltd, North Ryde (AU)

( * ) Notice: Subject to any disclaimer, the term of this patent is extended or adjusted under 35 U.S.C. 154(b) by 0 days.

(21) Appl. No.: 14/441,660

(22) PCT Filed: Nov. 26, 2013

(86) PCT No.: PCT/AU2013/001367
§ 371 (c)(1),
(2) Date: May 8, 2015

(87) PCT Pub. No.: WO2014/078913
PCT Pub. Date: May 30, 2014

(65) Prior Publication Data
US 2016/0017418 A1 Jan. 21, 2016

Related U.S. Application Data

(60) Provisional application No. 61/729,831, filed on Nov. 26, 2012.

(51) Int. Cl.
*C12Q 1/68* (2006.01)

(52) U.S. Cl.
CPC ......... *C12Q 1/6876* (2013.01); *C12Q 1/6851* (2013.01); *C12Q 1/6886* (2013.01); *C12Q 2600/154* (2013.01)

(58) Field of Classification Search
None
See application file for complete search history.

(56) References Cited

U.S. PATENT DOCUMENTS

| | | |
|---|---|---|
| 2008/0286778 A1 | 11/2008 | Lewin et al. |
| 2009/0004646 A1 | 1/2009 | Schuster et al. |
| 2010/0248228 A1 | 9/2010 | Wang et al. |
| 2012/0202202 A1 | 8/2012 | Wang et al. |
| 2012/0264618 A1 | 10/2012 | Nygren |

FOREIGN PATENT DOCUMENTS

WO 2012/034170 A1 3/2012

OTHER PUBLICATIONS

Strausberg et al, in Microarrays and Cancer Research, 2002, Warrington et al (eds.), Eaton Publishing, Westborough, MA, pp. xi-xvi.*

Notterman et al, in Microarrays and Cancer Research, 2002, Warrington et al (eds.), Eaton Publishing, Westborough, MA, pp. 81-111.*
Deiman et al., "Characteristics and Applications of Nucleic Acid Sequence-Based Amplification (NASBA)," *Molecular Biotechnology* 20:163-179, 2002.
Frommer et al., "A genomic sequencing protocol that yields a positive display of 5-methylcytosine residues in individual DNA strands," *Proc. Natl. Acad. Sci. USA* 89:1827-1831, Mar. 1992.
Gibson et al., "A Novel Method for Real Time Quantitative RT-PCR," *Genome Research* 6(10):995-1001, 1996.
Herman et al., "Methylation-specific PCR: A novel PCR assay for methylation status of CpG islands," *Proc. Natl. Acad. Sci. USA* 93:9821-9826, Sep. 1996.
Holland et al., "Detection of specific polymerase chain reaction product by utilizing the 5'→3' exonuclease activity of *Thermus aquaticus* DNA polymerase," *Proc. Natl. Acad. Sci. USA* 88:7276-7280, Aug. 1991.
"*Homo sapiens* colon adenocarcinoma hypermethylated (non-protein coding) (CAHM), non-coding RNA," NCBI Reference Sequence: NR_037593.1, from Bonal et al., "Normalization and subtraction: two approaches to facilitate gene discovery," *Genome Res.* 6(9): 791-806, 1996, retrieved from http://www.ncbi.nlm.nih.gov/nuccore/312836816?sat=17&satkey=25301813 on Feb. 17, 2014, 2 pages.
International Search Report, mailed Feb. 10, 2014, for corresponding International Application No. PCT/AU2013/001367, 8 pages.
Lee et al., "Allelic discrimination by nick-translation PCR with fluorogenic probes," *Nucleic Acids Research* 21(16):3761-3766, 1993.
Levenson et al., "The MethDet: a technology for biomarker development," *Expert Rev Mol Diagn* 11(8):807-812, Nov. 2011.
Markowitz et al., "Molecular Basis of Colorectal Cancer," *The New England Journal of Medicine* 361(25):2449-2460, Dec. 17, 2009.
Sadri et al., "Rapid analysis of DNA methylation using new restriction enzyme sites created by bisulfite modification," *Nucleic Acids Research* 24(24):5058-5059, 1996.
Weitzel, "Genetic Cancer Risk Assessment: Putting It All Together," *Cancer* 86:2483-2492, 1999.

(Continued)

*Primary Examiner* — James Martinell
(74) *Attorney, Agent, or Firm* — Seed IP Law Group LLP

(57) ABSTRACT

The present invention relates to a method of screening for the presence of methylated DNA in a biological sample by using multiple methylation-sensitive restriction endonucleases. More particularly, the present invention relates to a method of quantitatively screening for the level of one or more methylated genes of interest without the requirement that an undigested internal reference sample is used as a point of reference against which relative quantification is calculated. The present invention is useful in a range of applications including, but not limited to, providing a simpler and more accurate means to determine DNA methylation status, such as in the context of diagnosing or monitoring conditions characterised by changes to DNA methylation.

19 Claims, 2 Drawing Sheets

(56) References Cited

OTHER PUBLICATIONS

Xiong et al., "COBRA: a sensitive and quantitative DNA methylation assay," *Nucleic Acids Research* 25(12):2532-2534, 1997.
Zhao et al., "Quantification and application of the placental epigenetic signature of the RASSF1A gene in maternal plasma," *Prenat Diagn* 30:778-782, 2010.
DeGraves et al., "High-Sensitivity Quantitative PCR Platform," *BioTechniques* 34:106-115 (8 pages), 2003.
Adany et al., "Hypomethylation of the decorin proteoglycan gene in human colon cancer," *Biochem. J.* 276:301-306, 1991.
Ellinger et al., "CpG Island Hypermethylation in Cell-Free Serum DNA Identifies Patients With Localized Prostate Cancer," *The Prostate* 68:42-49, 2008.
Pedersen et al., "Discovery and Validation of a Novel DNA Methylation Biomarker for Colorectal Cancer With Application to Blood Testing," *Gastroenterology* 142(5), Supp. 1, pp. S-33, Apr. 18-May 22, 2012, 1 page.

\* cited by examiner

METHOD OF DETECTING METHYLATION

STATEMENT REGARDING SEQUENCE LISTING

The Sequence Listing associated with this application is provided in text format in lieu of a paper copy, and is hereby incorporated by reference into the specification. The name of the text file containing the Sequence Listing is 200226_402USPC_SEQUENCE_LISTING.txt. The text file is 2.6 KB, was created on Aug. 16, 2015, and is being submitted electronically via EFS-Web.

FIELD OF THE INVENTION

The present invention relates to a method of screening for the presence of methylated DNA in a biological sample. More particularly, the present invention relates to a method of quantitatively screening for the level of one or more methylated genes of interest without the requirement that an undigested internal reference sample is used as a point of reference against which relative quantification is calculated. The present invention is useful in a range of applications including, but not limited to, providing a simpler and more accurate means to determine DNA methylation status, such as in the context of diagnosing or monitoring conditions characterised by changes to DNA methylation.

BACKGROUND OF THE INVENTION

Bibliographic details of the publications referred to by author in this specification are collected alphabetically at the end of the description.

The reference in this specification to any prior publication (or information derived from it), or to any matter which is known, is not, and should not be taken as an acknowledgment or admission or any form of suggestion that that prior publication (or information derived from it) or known matter forms part of the common general knowledge in the field of endeavour to which this specification relates.

Colorectal cancer includes cancerous growths in the colon, rectum and appendix. With 655,000 deaths worldwide per year, it is the fourth most common form of cancer in the United States and the third leading cause of cancer-related death in the Western world. Colorectal cancers arise from adenomatous polyps in the colon. These mushroom-shaped growths are usually benign, but some develop into cancer over time. Localized colon cancer is usually diagnosed through colonoscopy.

Invasive cancers that are confined within the wall of the colon (TNM stages I and II) are curable with surgery. If untreated, they spread to regional lymph nodes (stage III), where up to 73% are curable by surgery and chemotherapy. Cancer that metastasizes to distant sites (stage IV) is usually not curable, although chemotherapy can extend survival, and in rare cases, surgery and chemotherapy together have seen patients through to a cure (Markowitz and Bertagnolli, 2009, *N. Engl. J. Med.* 361(25): 2449-60). Radiation is used with rectal cancer.

Colorectal cancer is preceded by adenomas. Adenomas are benign tumours, or neoplasms, of epithelial origin which are derived from glandular tissue or exhibit clearly defined glandular structures. Some adenomas show recognisable tissue elements, such as fibrous tissue (fibroadenomas) and epithelial structure, while others, such as bronchial adenomas, produce active compounds that might give rise to clinical syndromes.

Adenomas may progress to become an invasive neoplasm and are then termed adenocarcinomas. Accordingly, adenocarcinomas are defined as malignant epithelial tumours arising from glandular structures, which are constituent parts of many organs of the body. The term adenocarcinoma is also applied to tumours showing a glandular growth pattern. These tumours may be sub-classified according to the substances that they produce, for example mucus secreting and serous adenocarcinomas, or to the microscopic arrangement of their cells into patterns, for example papillary and follicular adenocarcinomas. These carcinomas may be solid or cystic (cystadenocarcinomas). Each organ may produce tumours showing a variety of histological types, for example the ovary may produce both mucinous and cystadenocarcinoma.

The symptoms of colorectal cancer depend on the location of tumor in the bowel, and whether is has metastasised. Unfortunately, many of the symptoms may occur in other diseases as well, and hence symptoms may not be conclusively diagnostic of colorectal cancer.

Local symptoms are more likely if the tumor is located closer to the anus. There may be a change in bowel habit (new-onset constipation or diarrhea in the absence of another cause), a feeling of incomplete defecation and reduction in diameter of stools. Tenesmus and change in stool shape are both characteristic of rectal cancer. Lower gastrointestinal bleeding, including the passage of bright red blood in the stool, may indicate colorectal cancer, as may the increased presence of mucus. Melena, black stool with a tarry appearance, normally occurs in upper gastrointestinal bleeding (such as from a duodenal ulcer), but is sometimes encountered in colorectal cancer when the disease is located in the beginning of the large bowl.

Colorectal cancer most commonly spreads to the liver. This may go unnoticed, but large deposits in the liver may cause jaundice and abdominal pain (due to stretching of the capsule). If the tumor deposit obstructs the bile duct, the jaundice may be accompanied by other features of biliary obstruction, such as pale stools.

Colorectal cancer can take many years to develop and early detection of colorectal cancer greatly improves the prognosis. Even modest efforts to implement colorectal cancer screening methods can result in a drop in cancer deaths. Despite this, colorectal cancer screening rates remain low. There are currently several different tests available for this purpose:

Digital rectal exam: The doctor inserts a lubricated, gloved finger into the rectum to feel for abnormal areas. It only detects tumors large enough to be felt in the distal part of the rectum but is useful as an initial screening test.

Faecal occult blood test: a test for blood in the stool. Two types of tests can be used for detecting occult blood in stools i.e. guaiac based (chemical test) and immunochemical. The sensitivity of immunochemical testing is superior to that of chemical testing without an unacceptable reduction in specificity (Weitzel J N (December 1999). "Genetic cancer risk assessment. Putting it all together". *Cancer* 86 (11 Suppl): 2483-92).

Endoscopy:
Sigmoidoscopy: A lit probe (sigmoidoscope) is inserted into the rectum and lower colon to check for polyps and other abnormalities.
Colonoscopy: A lit probe called a colonoscope is inserted into the rectum and the entire colon to look for polyps and other abnormalities that may be caused by cancer. A colonoscopy has the advantage that if polyps are found during the procedure they can be removed immediately. Tissue can also be taken for biopsy.

Double contrast barium enema (DCBE): First, an overnight preparation is taken to cleanse the colon. An enema containing barium sulfate is administered, then air is insufflated into the colon, distending it. The result is a thin layer of barium over the inner lining of the colon which is visible on X-ray films. A cancer or a precancerous polyp can be detected this way. This technique can miss the (less common) flat polyp.

Virtual colonoscopy replaces X-ray films in the double contrast barium enema (above) with a special computed tomography scan and requires special workstation software in order for the radiologist to interpret. This technique is approaching colonoscopy in sensitivity for polyps. However, any polyps found must still be removed by standard colonoscopy.

Standard computed axial tomography is an x-ray method that can be used to determine the degree of spread of cancer, but is not sensitive enough to use for screening. Some cancers are found in CAT scans performed for other reasons.

Blood tests: Measurement of the patient's blood for elevated levels of certain proteins can give an indication of tumor load. In particular, high levels of carcinoembryonic antigen (CEA) in the blood can indicate metastasis of adenocarcinoma. While these tests are frequently false positive or false negative, and are not recommended for screening, they can be useful to assess disease recurrence. CA19-9 and CA 242 biomarkers can indicate e-selectin related metastatic risks, help follow therapeutic progress, and assess disease recurrence. Recently, an assay for detection in plasma of methylated sequences of the Septin 9 gene has also become available to assist in diagnosis of colorectal cancer.

Positron emission tomography (PET) is a 3-dimensional scanning technology where a radioactive sugar is injected into the patient, the sugar collects in tissues with high metabolic activity, and an image is formed by measuring the emission of radiation from the sugar. Because cancer cells often have very high metabolic rates, this can be used to differentiate benign and malignant tumors. PET is not used for screening and does not (yet) have a place in routine workup of colorectal cancer cases.

Stool DNA testing is an emerging technology in screening for colorectal cancer. Premalignant adenomas and cancers shed DNA markers from their cells which are not degraded during the digestive process and remain stable in the stool. Capture, followed by PCR amplifies the DNA to detectable levels for assay.

High C-Reactive Protein levels as risk marker

Despite the existence of these tests, diagnosis remains problematic. Most of the more sensitive tests are quite invasive and expensive and therefore uptake by patients is low. Accordingly, the determination that changes to the methylation of certain genes is indicative of the development of large intestine neoplasms has been very significant since it provides a highly sensitive and reliable means of screening for the onset of large intestine neoplasms.

There are a variety of methods that are currently available to identify altered methylation sites in cancer cells. Analysis of DNA methylation patterns and 5-methylcyto sine distribution is commonly performed using bisulfite treatment (Frommer et al., *Proc. Natl. Acad. Sci. USA*, 89:1827-1831, 1992). Specifically, bisulfite treatment of DNA is used as a starting point for methylation analysis using a variety of techniques. These include methylation-specific PCR (MSP) (Herman et al., *Proc. Natl. Acad. Sci. USA*, 93:9821-9826, 1992) and restriction enzyme digestion of PCR products amplified from bisulfite-converted DNA (Sadri and Hornsby, *Nucl. Acids Res.* 24:5058-5059, 1996; Xiong and Laird, *Nucl. Acids Res.* 25:2532-2534, 1997). Sodium bisulfite treatment converts all unmethylated cytosines in the DNA to uracil by deamination, but leaves the methylated cytosine residues intact. Subsequent PCR amplification replaces the uracil residues with thymines and the 5-methylcytosine residues with cytosines. The resulting sequence difference can be detected using standard DNA sequence detection techniques, primarily by methylation specific PCR bisulfite DNA sequencing. However, there are disadvantages to bisulfite conversion based methods including the requirement for high starting DNA concentrations due to the relatively harsh actions of sodium bisulfite.

Another method for analysing changes in methylation patterns is a PCR-based process that involves digestion of native/wild type DNA with methylation-sensitive restriction enzymes prior to PCR amplification (Singer-Sam et al., *Nucleotide. Acids. Res.* 18:687, 1990). However, this method has a tendency to suffer from a high degree of false positive signals (i.e. that methylation is present) due to incomplete digestion of unmethylated DNA, which then is falsely amplified in a subsequent PCR reaction. Although there has been significant research performed in an effort to improve this method for screening purposes, in particular to reduce the incidence of false positives resulting from incomplete digestion, this technology has not been enabled to the point of eliminating the incidence of false positives. That is, although there have been improvements developed which reduce the extent of incomplete digestion, there has not been a method developed which reliably and routinely achieves complete digestion. Accordingly, to date, methods based on the use of methylation sensitive restriction endonucleases have necessitated the PCR analysis of both undigested and digested aliquots of the test sample where the test sample is assessed relative to this control, the readout which is obtained is actually relative in nature. There is therefore an ongoing need to develop improved methods which do not suffer from these limitations.

In work leading up to the present invention it has been determined that where methylation sensitive restriction endonuclease-related analysis of DNA methylation is based on the use of at least two methylation sensitive enzymes together with digestion at 4-6 pgDNA/unit of endonuclease/hour, a level of digestion is achieved which is effectively complete, meaning that PCR amplification will not result in detectable amplicons due to the presence of undigested DNA. Still further, where amplification is performed by quantitative PCR using primers which flank the methylation specific restriction endonuclease recognition sequence region, absolute quantification is achievable and the requirement to amplify an undigested internal control sample to calculate relative quantitative values is eliminated. This development has significant implications in terms of diagnostic utility since it provides not only a simpler and cheaper method for analysing DNA methylation but also a means of accurately obtaining absolute quantification.

SUMMARY OF THE INVENTION

Throughout this specification and the claims which follow, unless the context requires otherwise, the word "comprise", and variations such as "comprises" and "comprising", will be understood to imply the inclusion of a stated integer or step or group of integers or steps but not the exclusion of any other integer or step or group of integers or steps.

As used herein, the term "derived from" shall be taken to indicate that a particular integer or group of integers has originated from the species specified, but has not necessarily been obtained directly from the specified source. Further, as used herein the singular forms of "a", "and" and "the" include plural referents unless the context clearly dictates otherwise.

Unless otherwise defined, all technical and scientific terms used herein have the same meaning as commonly understood by one of ordinary skill in the art to which this invention belongs.

The subject specification contains nucleotide sequence information prepared using the programme PatentIn Version 3.5, presented herein after the bibliography. Each nucleotide sequence is identified in the sequence listing by the numeric indicator <210> followed by the sequence identifier (e.g. <210>1, <210>2, etc). The length, type of sequence (DNA, etc) and source organism for each sequence is indicated by information provided in the numeric indicator fields <211>, <212> and <213>, respectively. Nucleotide sequences referred to in the specification are identified by the indicator SEQ ID NO: followed by the sequence identifier (e.g. SEQ ID NO:1, SEQ ID NO:2, etc.). The sequence identifier referred to in the specification correlates to the information provided in numeric indicator field <400> in the sequence listing, which is followed by the sequence identifier (e.g. <400>1, <400>2, etc). That is SEQ ID NO:1 as detailed in the specification correlates to the sequence indicated as <400>1 in the sequence listing.

In one aspect there is provided a method of quantitatively screening for the methylation of a DNA region of interest in a biological sample, said method comprising:
(i) contacting DNA from said biological sample with two or more methylation-sensitive restriction endonucleases and digesting said DNA at 4-6 pg of said DNA per unit of said endonucleases per hour;
(ii) quantitatively amplifying the digested DNA sample of step (i) using one or more forward primers and one or more reverse primers, which primers are directed to DNA sequences flanking one or more methylation specific restriction endonucleases recognition sequence regions; and
(iii) quantifying the level of said methylated DNA region of interest.

In another aspect there is provided a method of quantitatively screening for the methylation of a DNA region of interest in a biological sample, said method comprising:
(i) contacting DNA from said biological sample with two or more methylation-sensitive restriction endonucleases and digesting said DNA at 4-6 pg of said DNA per unit of said endonucleases per hour;
(ii) quantitatively amplifying the digested DNA sample of step (i) using one or more forward primers and one or more reverse primers, which primers are directed to DNA sequences flanking one or more methylation specific restriction endonucleases recognition sequence regions; and
(iii) quantifying the level of said methylated DNA region of interest wherein said quantification does not require determining the ratio of the amplified DNA of step (ii) relative to a corresponding undigested sample.

In yet another aspect there is more particularly provided a method of quantitatively screening for the methylation of a gene of interest in a biological sample, said method comprising:
(i) contacting DNA from said biological sample with two or more methylation-sensitive restriction endonucleases and digesting said DNA at 4-6 pg of said DNA per unit of said endonucleases per hour;
(ii) quantitatively amplifying the digested DNA sample of step (i) using one or more forward primers and one or more reverse primers, which primers are directed to DNA sequences flanking one or more methylation specific restriction endonuclease recognition sequence regions; and
(iii) quantifying the level of said methylated gene region wherein said quantification does not require determining the ratio of the amplified DNA of step (ii) relative to a corresponding undigested sample.

In still another aspect there is provided a method of quantitatively screening for the methylation in one or more of the gene loci BCAT1, IKZF1, IRF4, GRASP and CAHM in a biological sample, said method comprising:
(i) contacting DNA from said biological sample with two or more methylation-sensitive restriction endonucleases and digesting said DNA at 4-6 pg of said DNA per unit of said endonucleases per hour;
(ii) quantitatively amplifying the digested DNA sample of step (i) using one or more forward primers and one or more reverse primers, which primers are directed to DNA sequences flanking one or more methylation specific restriction endonuclease recognition sequences; and
(iii) quantifying the level of said one or more methylated genes wherein said quantification does not require determining the ratio of the amplified DNA of step (ii) relative to a corresponding undigested sample.

In yet still another aspect there is a provided a method of quantitatively screening for the methylation of a DNA region of interest in a biological sample, said method comprising:
(i) extracting the DNA from said biological sample and establishing the concentration of total DNA present in said sample;
(ii) contacting DNA from said biological sample with two or more methylation-sensitive restriction endonucleases and digesting said DNA at 4-6 pg of said DNA per unit of said endonucleases per hour;
(iii) quantitatively amplifying the digested DNA sample of step (ii) using one or more forward primers and one or more reverse primers, which primers are directed to DNA sequences flanking one or more methylation specific restriction endonuclease recognition sequences; and
(iv) quantifying the level of said methylated DNA region of interest wherein said quantification does not require determining the ratio of the amplified DNA of step
(iii) relative to a corresponding undigested sample.

In still yet another aspect there is therefore provided a method of quantitatively screening for the methylation of a gene of interest in a biological sample, said method comprising:
(i) establishing the concentration of total DNA present in said sample;
(ii) contacting 1-10 ng of DNA from said biological sample with two or more methylation-sensitive restriction endonucleases, wherein one of said enzymes is a Type IIe enzyme, and digesting said DNA at 4-6 pg of said DNA per unit of said endonucleases per hour;

(iii) quantitatively amplifying the digested DNA sample of step (ii) using one or more forward primers and one or more reverse primers, which primers are directed to DNA sequences flanking one or more selected methylation specific restriction endonuclease recognition sequence regions; and
(iv) quantifying the level of said methylated gene wherein said quantification does not require determining the ratio of the amplified DNA of step (iii) relative to a corresponding undigested sample.

In a further aspect there is therefore provided a method of quantitatively screening for the level of methylation of one or more of BCAT1, IKZF1, IRF4, GRASP and CAHM in a biological sample, said method comprising:
(i) establishing the concentration of total DNA present in said sample;
(ii) contacting 1-10 ng of DNA from said biological sample with HpaII and HhaI and digesting said DNA at 4-6 pg of said DNA per unit of said endonucleases per hour;
(iii) quantitatively amplifying the digested DNA sample of step (ii) using one or more forward primers and one or more reverse primers, which primers are directed to DNA regions flanking a one or more selected HpaII and HhaI recognition sequence regions; and
(iv) quantifying the level of said methylated BCAT1, IKZF1, IRF4, GRASP and/or CAHM wherein said quantification does not require determining the ratio of the amplified DNA of step (iii) relative to a corresponding undigested sample.

In another further aspect there is provided a method of quantitatively screening for the level of methylation of one or more of BCAT1, IKZF1, IRF4, GRASP and CAHM in a biological sample, said method comprising:
(i) establishing the concentration of total DNA present in said sample;
(ii) contacting 1-10 ng of DNA from said biological sample with HpaII, HhaI and ExoI and digesting said DNA at 4-6 pg of said DNA per unit of said endonucleases per hour;
(iii) quantitatively amplifying the digested DNA sample of step (ii) using one or more forward primers and one or more reverse primers, which primers are directed to DNA regions flanking one or more selected HpaII and HhaI recognition sequence regions; and
(iv) quantifying the level of said methylated BCAT1, IKZF1, IRF4, GRASP and/or CAHM wherein said quantification does not require determining the ratio of the amplified DNA of step (iv) relative to a corresponding undigested sample.

In yet another further aspect, the method of the present invention is directed to screening for methylated GRASP using HhaI/HpaII digestion, the amplification step is performed using:

```
(i)
Forward primer:
                                    (SEQ ID NO: 2)
5'-CAAGTTGAAGGTCCGAGAGC;
and (ii)
Reverse primer:
                                    (SEQ ID NO: 3)
5'-CGCACTTCCTCAGAGTGAGA.
```

In still another further aspect the method of the present invention is directed to screening for methylated BCAT1 using HhaI/HpaII digestion, the amplification step is performed using:

```
(i)
Forward primer:
                                    (SEQ ID NO: 4)
5'-AGATCCCAAGGGTCGTAGC;
and (ii)
Reverse primer:
                                    (SEQ ID NO: 5)
5'-ACTGCCCCAGGTCTTGCT.
```

In yet still another further aspect, the method of the present invention is directed to screening for methylated IKZF1 using HhaI/HpaII digestion, the amplification step is performed using:

```
(i)
Forward primer:
                                    (SEQ ID NO: 6)
5'-GGAGTTGCGGCTGAGAC;
and (ii)
Reverse primer:
                                    (SEQ ID NO: 7)
5'-AGAGCGGGACACGGAGA.
```

DETAILED DESCRIPTION OF THE INVENTION

Figure 1:
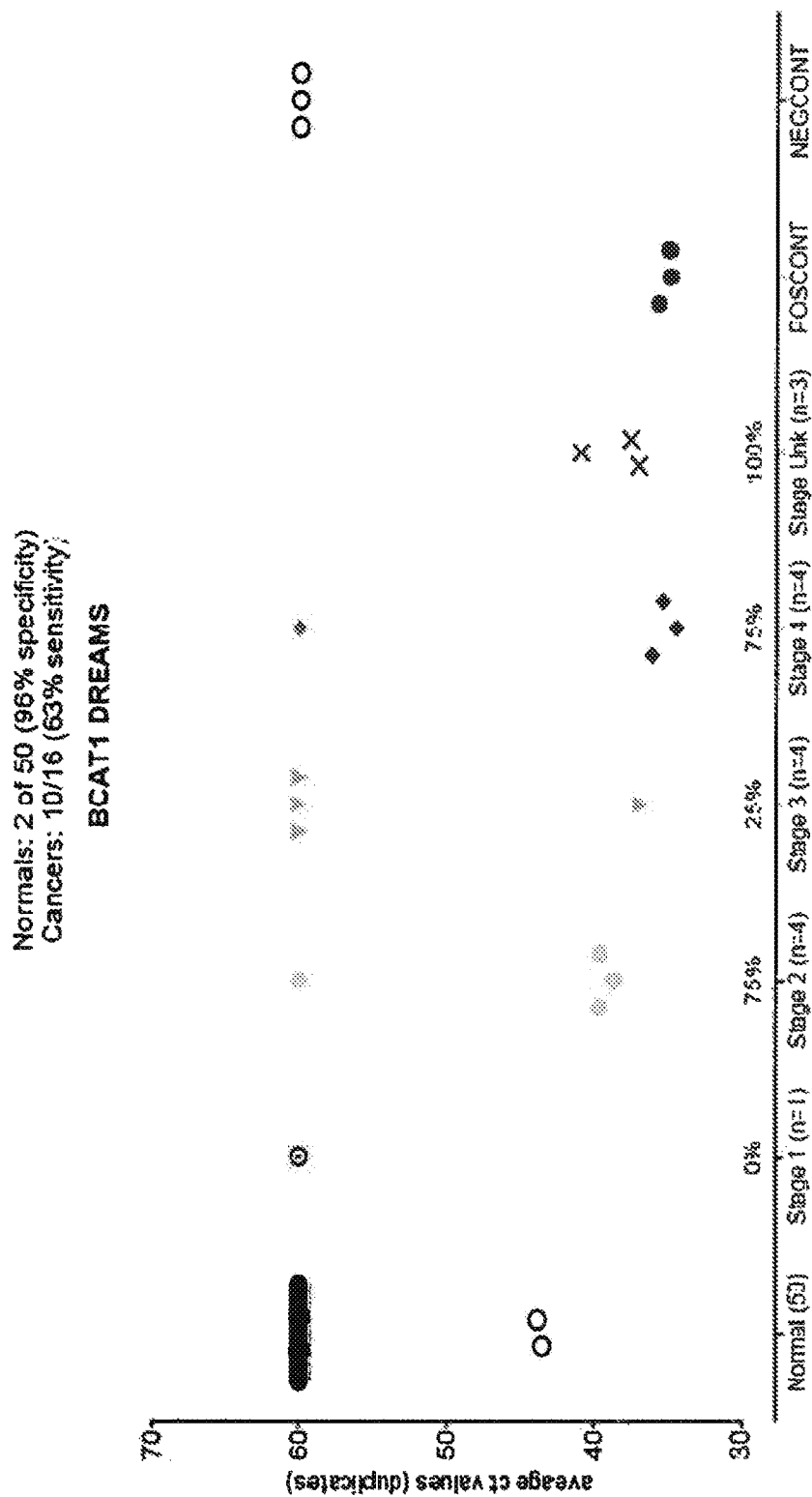
FIG. 1 is a graphical representation of methylation levels measured in BCAT1 gene locus using the method. Digestion with Restriction Enzymes to Assay Methylation Status [DREAMS] was applied to circulating DNA isolated from 4 mL of blood plasma. The concentration of the extracted DNA was determined by quantitative real-time PCR and 3.6 ng DNA was digested for 72 hours with HhaI and HpaII. The digestion mixture was then analysed in BCAT1 DREAMS quantitative PCR (1.6 ng per duplicate PCR reaction). No signal was artificially assigned the value "60". The figure shows the average Cycle threshold [Ct] values measured in 1.6 ng of digested DNA isolated from blood plasma from colonoscopy confirmed patients including 50 normals (open circles) and 16 colorectal cancers (dotted circles: Stage 1, n=1; yellow: Stage 2, n=4; orange: Stage 3, n=4; red: Stage 4, n=4; crosses: unknown cancer stages, n=3). POSCONT: positive control for methylation detection. 4 mL plasma from healthy donors spiked with 5 ng of fully methylated DNA (Millipore). NEGCONT: negative control for methylation detection. 4 mL of plasma from healthy donors. Samples were called positive if a Ct signal was obtained. The BCAT1 DREAMS assay demonstrated a specificity of 96% and a sensitivity of 63%.
Figure 2:
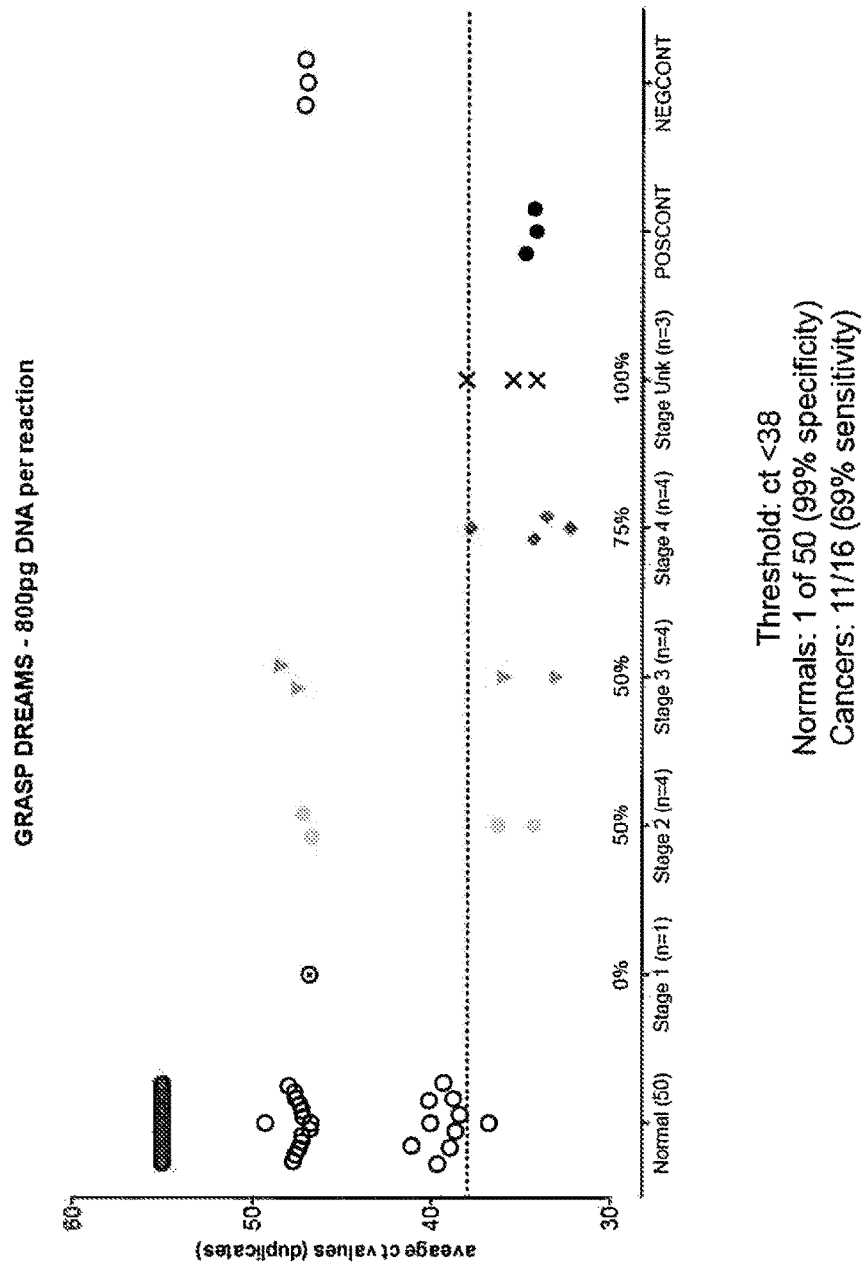
FIG. 2 is a graphical representation of methylation levels measured in GRASP gene locus using the method described in FIG. 1 legend. A total of 3.6 ng of extracted plasma DNA was digested for 72 hours with HhaI and HpaII. The digestion mixture was then analysed in GRASP DREAMS quantitative PCR (1.6 ng per duplicate PCR reaction). No signal was artificially assigned the value "55". The figure shows the average cycle threshold [Ct] values measured in 1.6 ng of digested native DNA isolated from blood plasma from colonoscopy confirmed patients including 50 normals (open circles) and 16 colorectal cancers (dotted circles: Stage 1, n=1; yellow: Stage 2, n=4; orange: Stage 3, n=4; red: Stage 4, n=4; crosses: unknown cancer stages, n=3). Samples were called positive with ct values <38. POSCONT: positive control for methylation detection. 4 mL plasma from healthy donors spiked with 5 ng of fully methylated DNA (Millipore). NEGCONT: negative control for methylation detection. 4 mL of plasma from healthy donors. The GRASP DREAMS assay demonstrated a specificity of 99% and a sensitivity of 69%.

The present invention is predicated, in part, on the determination that complete digestion by methylation specific restriction endonucleases can be effectively achieved where digestion is performed with two or more methylation specific restriction endonucleases at 4-6 pgDNA/unit of endonucleases/hr. Still further, by designing the amplification step so as to use primers flanking the restriction endonuclease recognition sequence regions, absolute quantification is achievable and the need for quantification to be performed in a relative manner against an internal undigested control sample is eliminated.

Accordingly, in one aspect there is provided a method of quantitatively screening for the methylation of a DNA region of interest in a biological sample, said method comprising:
(i) contacting DNA from said biological sample with two or more methylation-sensitive restriction endonucleases and digesting said DNA at 4-6 pg of said DNA per unit of said endonucleases per hour;
(ii) quantitatively amplifying the digested DNA sample of step (i) using one or more forward primers and one or more reverse primers, which primers are directed to DNA sequences flanking one or more methylation specific restriction endonucleases recognition sequence regions; and
(iii) quantifying the level of said methylated DNA region of interest.

More particularly, there is provided a method of quantitatively screening for the methylation of a DNA region of interest in a biological sample, said method comprising:
(i) contacting DNA from said biological sample with two or more methylation-sensitive restriction endonucleases and digesting said DNA at 4-6 pg of said DNA per unit of said endonucleases per hour;
(ii) quantitatively amplifying the digested DNA sample of step (i) using one or more forward primers and one or more reverse primers, which primers are directed to DNA sequences flanking one or more methylation specific restriction endonucleases recognition sequence regions; and
(iii) quantifying the level of said methylated DNA region of interest wherein said quantification does not require determining the ratio of the amplified DNA of step (ii) relative to a corresponding undigested sample.

In one embodiment, step (ii) is performed in the presence of one or more TaqMan probes.

Reference to a "DNA region of interest" should be understood as a reference to any region of DNA, the methylation status of which is sought to be analysed. This may be, for example, a gene, part of a gene, an intergenic region, a promoter or mitochondrial DNA. To this end, reference to "gene" should be understood as a reference to a DNA molecule which codes for a protein product, whether that be a full length protein or a protein fragment. It should be understood, however, that there are some genes or gene regions, which have been identified which are not known to necessarily produce a protein product. Reference to "gene" herein should therefore be understood to include reference to both types of genes. In terms of genomic DNA, the gene will generally be expected to include both intron and exon regions. The subject DNA region of interest may also be a non-coding portion of genomic DNA which is not known to be associated with any specific gene (such as the commonly termed "junk" DNA regions). The DNA target region of interest may also be any region of genomic DNA produced by recombination, either between 2 regions of genomic DNA or 1 region of genomic DNA and a region of foreign DNA such as a virus or an introduced sequence. The DNA which is the subject of analysis need not necessarily be genomic DNA, although it is generally understood that DNA produced through recombinant techniques, such as cDNA or DNA copies of non-coding RNAs, is not methylated. Nevertheless, the present invention should be understood to extend to the analysis of any source of DNA which may be methylated.

Without limiting the present invention to any one theory or mode of action, DNA methylation is universal in bacteria, plants, and animals. DNA methylation is a type of chemical modification of DNA that is stable over rounds of cell division but does not involve changes in the underlying DNA sequence of the organism. Chromatin and DNA modifications are two important features of epigenetics and play a role in the process of cellular differentiation, allowing cells to stably maintain different characteristics despite containing the same genomic material. In eukaryotic organisms DNA methylation occurs only at the number 5 carbon of the cytosine pyrimidine ring. In mammals, DNA methylation occurs mostly at the number 5 carbon of the cytosine of a CpG dinucleotide. CpG dinucleotides comprise approximately 1% of the human genome.

70-80% of all CpGs are methylated. CpGs may be grouped in clusters called "CpG islands" that are present in the 5'-end of regulatory regions of many genes and are frequently unmethylated. In many disease processes such as cancer, gene promoters and/or CpG islands acquire abnormal hypermethylation, which is associated with heritable transcriptional silencing. DNA methylation may impact the transcription of genes in two ways. First, the methylation of DNA may itself physically impede the binding of transcriptional proteins to the gene, thus blocking transcription. Second, methylated DNA may be bound by proteins known as Methyl-CpG-binding domain proteins (MBDs). MBD proteins then recruit additional proteins to the locus, such as histone deacetylases and other chromatin remodelling proteins that can modify histones, thereby forming compact, inactive chromatin termed silent chromatin. This link between DNA methylation and chromatin structure is very important. In particular, loss of Methyl-CpG-binding Protein 2 (MeCP2) has been implicated in Rett syndrome and Methyl-CpG binding domain protein 2 (MBD2) mediates the transcriptional silencing of hypermethylated genes in cancer.

In humans, the process of DNA methylation is carried out by three enzymes, DNA methyltransferase 1, 3a and 3b (DNMT1, DNMT3a, DNMT3b). It is thought that DNMT3a and DNMT3b are the de novo methyltransferases that set up DNA methylation patterns early in development. DNMT1 is the proposed maintenance methyltransferase that is responsible for copying DNA methylation patterns to the daughter strands during DNA replication. DNMT3L is a protein that is homologous to the other DNMT3s but has no catalytic activity. Instead, DNMT3L assists the de novo methyltransferases by increasing their ability to bind to DNA and stimulating their activity. Finally, DNMT2 has been identified as an "enigmatic" DNA methyltransferase homolog, containing all 10 sequence motifs common to all DNA methyltransferases; however, DNMT2 may not methylate DNA but instead has been shown to methylate a small RNA.

The term "methylation" should therefore be understood to mean the presence of a methyl group added by the action of a DNA methyl transferase enzyme to a cytosine base or bases in a region of nucleic acid, e.g. genomic DNA.

In one embodiment, said DNA region of interest is a gene.

According to this embodiment there is more particularly provided a method of quantitatively screening for the methylation of a gene of interest in a biological sample, said method comprising:
(i) contacting DNA from said biological sample with two or more methylation-sensitive restriction endonucleases and digesting said DNA at 4-6 pg of said DNA per unit of said endonucleases per hour;
(ii) quantitatively amplifying the digested DNA sample of step (i) using one or more forward primers and one or more reverse primers, which primers are directed to DNA sequences flanking one or more methylation specific restriction endonuclease recognition sequence regions; and
(iii) quantifying the level of said methylated gene region wherein said quantification does not require determining the ratio of the amplified DNA of step (ii) relative to a corresponding undigested sample.

In another embodiment, said gene is a mammalian gene.

In a further embodiment, said gene is a large intestine neoplasm marker and, more particularly, BCAT1, IKZF1, CAHM, GRASP or IRF4.

These genes are specified herein by reference to both gene name and a set of human chromosomal coordinates. Both the gene names and the chromosomal coordinates would be well known to, and understood by, the person of skill in the art. The chromosomal coordinates for regions assayed on Nimblegen promoter tiling arrays correspond to the Hg18 version of the genome, while those describing the associated gene symbol correspond to the Hg19 version of the genome. In general, a gene can be routinely identified by reference to its name, via which both its sequences and chromosomal location can be routinely obtained, or by reference to its chromosomal coordinates, via which both the gene name and its sequence can also be routinely obtained.

Reference to "genes" should be understood as a reference to all forms of these molecules and to fragments or variants thereof. As would be appreciated by the person skilled in the art, some genes are known to exhibit allelic variation between individuals or single nucleotide polymorphisms. SNPs encompass insertions and deletions of varying size and simple sequence repeats, such as dinucleotide and trinucleotide repeats. Variants include nucleic acid sequences from the same region sharing at least 90%, 95%, 98%, 99% sequence identity i.e. having one or more deletions, additions, substitutions, inverted sequences etc. relative to the genes described herein. Accordingly, the present invention should be understood to extend to such variants which, in terms of the present diagnostic applications, achieve the same outcome despite the fact that minor genetic variations between the actual nucleic acid sequences may exist between individuals. The present invention should therefore be understood to extend to all forms of DNA which arise from any other mutation, polymorphic or allelic variation.

The Hg19 chromosomal coordinates corresponding to the genes detailed above are as follows:
(1) BCAT: chr12:24962958 . . . 25102393
(2) IKZF1: chr7:50344378 . . . 50472798
(3) IRF4: chr6:391739 . . . 411443;
(4) GRASP: chr12:52400748 . . . 52409671; and
(5) CAHM: chr6:163834097 . . . 163834982.

Reference to these genes should be understood to include 5 kb upstream of the transcription start site of each of these genes.

As will be discussed in more detail hereafter, the method of the present invention can be applied to screening for the methylation of one gene or else it can be adapted to screen a given biological sample for the methylation of more than one gene either via separate aliquots of DNA from the original biological sample or in the context of a single aliquot which is amplified using a multiplexed amplification method (for example by using fluorescently labelled probes such as TaqMan hydrolysis or Molecular Beacon probes).

According to this embodiment there is provided a method of quantitatively screening for the methylation in one or more of the gene loci BCAT1, IKZF1, IRF4, GRASP and CAHM in a biological sample, said method comprising:
(i) contacting DNA from said biological sample with two or more methylation-sensitive restriction endonucleases and digesting said DNA at 4-6 pg of said DNA per unit of said endonucleases per hour;
(ii) quantitatively amplifying the digested DNA sample of step (i) using one or more forward primers and one or more reverse primers, which primers are directed to DNA sequences flanking one or more methylation specific restriction endonuclease recognition sequences; and
(iii) quantifying the level of said one or more methylated genes wherein said quantification does not require determining the ratio of the amplified DNA of step (ii) relative to a corresponding undigested sample.

The DNA which is tested in accordance with the method of the present invention is isolated from a biological sample. Reference to a "biological sample" should be understood as a reference to any sample of biological material derived from any source, such as animal, plant or bacterial, including but not limited to, cellular material, biofluids (e.g. blood or plasma), faeces, tissue biopsy specimens, surgical specimens or fluid which has been introduced into the body of an animal and subsequently removed (such as, for example, the solution retrieved from an enema wash). The biological sample which is tested according to the method of the present invention may be tested directly or may require some form of treatment prior to testing. For example, a biopsy or surgical sample may require homogenisation prior to testing. Alternatively, a cell sample may require permeabilisation prior to testing. Further, to the extent that the biological sample is not in liquid form, (if such form is required for testing) it may require the addition of a reagent, such as a buffer, to mobilise the sample.

To the extent that the DNA region of interest is present in a biological sample, the biological sample may be directly tested or else all or some of the nucleic acid present in the biological sample may be isolated prior to testing. In yet another example, the sample may be partially purified or otherwise enriched prior to analysis. For example, to the extent that a biological sample comprises a very diverse cell population, it may be desirable to enrich for a sub-population of particular interest. It is within the scope of the present invention for the target biological sample or molecules derived therefrom to be treated prior to testing, for example, inactivation of live virus. It should also be understood that the biological sample may be freshly harvested or it may have been stored (for example by freezing) prior to testing or otherwise treated prior to testing (such as by undergoing culturing).

The choice of what type of sample is most suitable for testing in accordance with the method disclosed herein will be dependent on the nature of the situation. To the extent that one is screening for the onset or predisposition to the onset of a large intestine neoplasm, for example, said sample is preferably a faecal (stool) sample, enema wash, surgical resection, tissue biopsy or blood sample (e.g. whole blood, serum, buffy coat or plasma)

More preferably, said biological sample is a blood sample, biopsy sample or stool sample.

As detailed hereinbefore, the method of the present invention is predicated on the determination that a quantitative readout of DNA methylation can be achieved where one can achieve complete DNA digestion by methylation sensitive restriction endonucleases followed by amplification using primers designed to flank the methylation specific restriction endonuclease recognition sequence. This determination enables the skilled person to dispense with the analysis of an internal undigested sample against which the test results obtained using prior art methods are analysed. These prior art methods provide only a relative readout regarding methylation levels. However, since the method of the present invention enables complete digestion to be achieved, the application of a quantitative amplification method which is based on the use of amplification primers directed to the DNA flanking the methylation specific restriction endonuclease recognition sequence enables absolute quantification to occur. Reference to "complete" digestion within the context of the method of the present invention should be understood as a reference to a level of digestion efficiency which results in there being no detectable PCR signal from the amplification of DNA which has not been fully digested.

Accordingly, it would be appreciated by the skilled person that there may be some degree of incomplete digestion but this will be so insignificant that this incompletely digested DNA will not result in a detectable PCR signal when using the PCR method of the present invention. In this situation, the DNA digestion is thereby regarded as effectively complete. Still further, this significant improvement in the efficiency of the digestion step has enabled the testing of very low quantities of DNA, such as as low as 1 ng. From the point of view of harvesting sufficient biological material for testing, this is very significant.

To this end, in one embodiment the DNA of the biological sample is preferably extracted by any suitable extraction method and the concentration of total DNA present in the sample is established. Methods of achieving this would be well known to the person of skill in the art and include, for example, phenol/chloroform extraction, cesium chloride gradients, CHELEX or silica column or bead methods. By virtue of extracting and establishing the concentration of the DNA present in the biological sample of interest, there is facilitated the ability to perform the method of the present invention on very low starting concentrations of DNA.

Accordingly, in one embodiment, there is a provided a method of quantitatively screening for the methylation of a DNA region of interest in a biological sample, said method comprising:
(i) extracting the DNA from said biological sample and establishing the concentration of total DNA present in said sample;
(ii) contacting DNA from said biological sample with two or more methylation-sensitive restriction endonucleases and digesting said DNA at 4-6 pg of said DNA per unit of said endonucleases per hour;
(iii) quantitatively amplifying the digested DNA sample of step (ii) using one or more forward primers and one or more reverse primers, which primers are directed to DNA sequences flanking one or more methylation specific restriction endonuclease recognition sequences; and
(iv) quantifying the level of said methylated DNA region of interest wherein said quantification does not require determining the ratio of the amplified DNA of step (iii) relative to a corresponding undigested sample.

In one embodiment, said DNA region of interest is a gene.

In another embodiment, 1-20 ng of the DNA extracted in step (i) is subjected to the digestion of step (ii). In another embodiment, 1-15 ng or 1-10 ng of DNA is used. Most particularly, one can use 2 ng, 3 ng, 4 ng, 5 ng, 6 ng, 7 ng, 8 ng or 9 ng of DNA.

Once the sample DNA is ready for testing, it is digested with two or more methylation sensitive restriction endonucleases. Reference to a "methylation sensitive restriction endonuclease" should be understood as a reference to a restriction endonuclease, the DNA cleavage activity of which is blocked or impaired when a particular base within its DNA recognition sequence is methylated. Accordingly, unmethylated DNA is cleaved and is therefore unable to be amplified by primers designed to amplify across the endonuclease cleavage site. Only methylated DNA will remain intact and thereby generate an amplification product.

As would be appreciated by the skilled person, this method is therefore dependent upon the selection and use of enzymes for which the relevant recognition sequence is present in the DNA region of interest. Since methylation specific restriction endonucleases are very well known and characterised, the selection of an appropriate endonuclease to enable analysis of the gene of interest is well within the skill of the person in the art. For example, detailed in Table 1, below, is an exemplary list of methylation specific restriction endonucleases together with the relevant DNA recognition sequence for each enzyme.

TABLE 1

| Enzyme | Sequence |
| --- | --- |
| AatII | GACGT/C |
| AccII | CG/CG |
| AciI | CCGC |
| AclI | AA/CGTT |
| AfeI | AGC/GCT |
| AgeI | A/CCGGT |
| AgeI-HF™ | A/CCGGT |
| AgeI-HF™RE-Mix® | A/CCGGT |
| Aor13HI | T/CCGGA |
| Aor51HI | AGC/GCT |
| AscI | GG/CGCGCC |
| AscI RE-Mix® | GG/CGCGCC |
| AsiSI | GCGAT/CGC |
| AvaI | C/YCGRG |
| BceAI | ACGGC |
| BmgBI | CACGTC |
| BsaAI | YAC/GTR |

TABLE 1-continued

| Enzyme | Sequence |
| --- | --- |
| BsaHI | GR/CGYC |
| BsiEI | CGRY/CG |
| BsiWI | C/BTACG |
| BsmBI | CGTCTC |
| BspDI | AT/CGAT |
| BspT104I | TT/CGAA |
| BsrFI | R/CCGGY |
| BssHII | G/CGCGC |
| BstBI | TT/CGAA |
| BstUI | CG/CG |
| Cfr10I | R/CCGGY |
| ClaI | AT/CGAT |
| CpoI | CG/GWCCG |
| EagI | C/GGCCG |
| EagI-HF™ | C/GGCCG |
| Eco52I | C/GGCCG |
| FauI | CCCGC |
| FseI | GGCCGG/CC |
| FspI | TGC/GCA |
| HaeII | RGCGC/Y |
| HapII | C/CGG |
| HgaI | GACGC |
| HhaI | GCG/C |
| HinP1I | G/CGC |
| HpaII | C/CGG |
| Hpy99I | CGWCG/ |
| HpyCH4IV | A/CGT |
| KasI | G/GCGCC |
| MluI | A/CGCGT |
| NaeI | GCC/GGC |
| NarI | GG/CGCC |
| NgoMIV | G/CCGGC |
| NotI | GC/GGCCGC |
| NotI-HF™RE-Mix® | GC/GGCCGC |
| NotI-HF™ | GC/GGCCGC |
| NruI | TCG/CGA |
| NsbI | TGC/GCA |
| Nt.BsmAI | GTCTC |
| Nt.CviPII | CCD |

TABLE 1-continued

| Enzyme | Sequence |
| --- | --- |
| PaeR7I | C/TCGAG |
| PmaCI | CAC/GTG |
| PM1I | CAC/GTG |
| Psp1406I | AA/CGTT |
| PvuI | CGAT/CG |
| PvuI-HF™ | CGAT/CG |
| RsrII | CG/GWCCG |
| SacII | CCGC/GG |
| SalI | G/TCGAC |
| SalI-HF™RE-Mix® | G/TCGAC |
| SalI-HF™ | G/TCGAC |
| SfoI | GGC/GCC |
| SgrAI | CR/CCGGYG |
| SmaI | CCC/GGG |
| SnaBI | TAC/GTA |
| TspMI | C/CCGGG |
| ZraI | GAC/GTC |

In terms of selecting the cocktail of enzymes for use in any given situation, in addition to selecting enzymes for which the recognition sequences are present in the gene of interest, it is particularly useful if the recognition sequences of any two or more enzymes are proximally located within a subregion of the gene of interest. This is useful from the point of view of amplification since it minimises the length of DNA between the outermost 5' and 3' recognition sequences, thereby minimising the size of the intact DNA fragment that is required to be present in the sample in order for the method to work. This enables sensitive analysis of heavily fragmented DNA such as that found in circulating cell free DNA. As detailed hereinbefore, since methylation specific restriction endonucleases are well known and characterised, in particular in the context of their recognition sequences, selecting an appropriate cocktail of two or more enzymes for use with a specific gene of interest is well within the skill of the person in the art.

To this end, reference to the subject primers being directed to DNA regions "flanking" the "methylation specific restriction endonuclease recognition sequence region" should be understood as a reference to the use of one or more forward and reverse primers which are proximally located 5'-of and 3'-of, respectively, to the subregion of the target DNA which comprises the recognition sequences. By "proximally" is meant that the primer hybridisation sites need not be immediately adjacent to the outermost recognition sequences but are located so as to enable amplification of the recognition sequence region without amplifying unnecessarily large sections of DNA falling outside this region. In this regard, the forward primers may be located upstream of the relevant endonuclease cut site and the reverse primers downstream of the relevant endonuclease cut site, such that they amplify across the cut site, or they may hybridise across the cut site, such that they will only hybridise to DNA which has not been cut.

It should be appreciated that where the two or more enzymes are isoschizomers, and therefore cut at the same recognition sequence, the relevant amplification region will comprise only one recognition sequence and the forward and reverse primers will therefore be designed to hybridise to DNA sequences which flank this recognition sequence region. Where methylation specific restriction endonucleases are used which cut at different recognition sequences, the subject "methylation specific restriction endonuclease recognition sequence region" should be understood to refer to the gene subregion within which the recognition sequences are clustered. In this regard, in one embodiment the two or more methylation specific restriction endonucleases are selected such that if they are not isoschizomers, they are nevertheless specific to recognition sequences which are located proximally to one another so as to minimise the size of the amplicon which would be generated where methylation exists.

The subject primers are said to "flank" this methylation specific restriction endonuclease recognition sequence region where they are designed to hybridise to DNA sequences which are located 5' and 3' to the outer ends of the cluster of recognition sequences of interest or which hybridise across the outer 5' and 3' cut sites. Although it would be appreciated that any one or more of the methylation specific restriction endonucleases may cut at a variety of positions across the full length of the gene, the skilled person may elect to seek to amplify the whole gene, in which case the "selected" methylation specific restriction endonuclease recognition sequence region is effectively the whole gene. Alternatively, the skilled person may elect a specific subregion within which one or more recognition sequences are clustered and amplify only this smaller region (and not any other recognition sequences present in other parts of the gene). In this case, this smaller subregion is the "selected" methylation specific restriction endonuclease recognition sequence region.

As detailed hereinbefore, the method of the present invention is predicated on the determination that a combination of two or more of said methylation specific restriction endonucleases together with digestion at 4-6 pg of said DNA per unit of said endonucleases per hour achieves complete digestion of the DNA under analysis. This finding is particularly significant when one considers that it had previously been taught that not all methylation sensitive restriction endonucleases are suitable for use in this type of application. In particular the Type IIe enzymes, such as HpaII, were understood to create problems in that they were unable to effect complete digestion. Accordingly, a background of undigested DNA was to be expected (Levenson & Melnikov, *Expert Rev. Molecule. Diagn.* 11(8):807-812, 2011). The method of the present invention, however, enables the use of any methylation sensitive restriction endonuclease.

In one embodiment of the present invention the two or more methylation specific restriction endonucleases include at least one Type IIe enzyme, more particularly HpaII.

According to this embodiment there is therefore provided a method of quantitatively screening for the methylation of a gene of interest in a biological sample, said method comprising:
(i) establishing the concentration of total DNA present in said sample;
(ii) contacting 1-10 ng of DNA from said biological sample with two or more methylation-sensitive restriction endonucleases, wherein one of said enzymes is a Type IIe enzyme, and digesting said DNA at 4-6 pg of said DNA per unit of said endonucleases per hour;
(iii) quantitatively amplifying the digested DNA sample of step (ii) using one or more forward primers and one or more reverse primers, which primers are directed to DNA sequences flanking one or more selected methylation specific restriction endonuclease recognition sequence regions; and
(iv) quantifying the level of said methylated gene wherein said quantification does not require determining the ratio of the amplified DNA of step (iii) relative to a corresponding undigested sample.

In another embodiment, said Type IIe enzyme is HpaII.

In still another embodiment, the digestion step is performed using the methylation specific restriction endonucleases HpaII and HhaI together with the single-stranded exonuclease, ExoI.

In yet still another embodiment, the digestion step is performed using the methylation specific restriction endonucleases HpaII, HhaI and ExoI.

In accordance with these embodiments, in yet still a further embodiment said gene is BCAT1, IKZF1, IRF4, GRASP or CAHM.

According to this embodiment there is therefore provided a method of quantitatively screening for the level of methylation of one or more of BCAT1, IKZF1, IRF4, GRASP and CAHM in a biological sample, said method comprising:
(i) establishing the concentration of total DNA present in said sample;
(ii) contacting 1-10 ng of DNA from said biological sample with HpaII and HhaI and digesting said DNA at 4-6 pg of said DNA per unit of said endonucleases per hour;
(iii) quantitatively amplifying the digested DNA sample of step (ii) using one or more forward primers and one or more reverse primers, which primers are directed to DNA regions flanking a one or more selected HpaII and HhaI recognition sequence regions; and
(iv) quantifying the level of said methylated BCAT1, IKZF1, IRF4, GRASP and/or CAHM wherein said quantification does not require determining the ratio of the amplified DNA of step (iii) relative to a corresponding undigested sample.

In still another embodiment there is provided a method of quantitatively screening for the level of methylation of one or more of BCAT1, IKZF1, IRF4, GRASP and CAHM in a biological sample, said method comprising:
(i) establishing the concentration of total DNA present in said sample;
(ii) contacting 1-10 ng of DNA from said biological sample with HpaII, HhaI and ExoI and digesting said DNA at 4-6 pg of said DNA per unit of said endonucleases per hour;
(iii) quantitatively amplifying the digested DNA sample of step (ii) using one or more forward primers and one or more reverse primers, which primers are directed to DNA regions flanking one or more selected HpaII and HhaI recognition sequence regions; and
(iv) quantifying the level of said methylated BCAT1, IKZF1, IRF4, GRASP and/or CAHM wherein said quantification does not require determining the ratio of the amplified DNA of step (iii) relative to a corresponding undigested sample.

Reference to a "methylation specific restriction endonuclease" should be understood as a reference to all forms of this enzyme including any isoforms which arise from alternative splicing of the subject enzyme's mRNA or allelic or polymorphic variants. Digestion of the DNA with methylation specific restriction endonucleases is required to proceed for a period of time which is based on the ratio of 4-6 pg of said DNA per unit of said endonucleases per hour. Reference to the "unit" of said endonucleases should be understood as a reference to the total units of activity of the endonuclease cocktail which has been selected for use. The unit activity of each endonuclease is defined by the manufacturer as the amount of enzyme required to digest a specified amount of a model DNA substrate (e.g., 1 µg lambda phage DNA) in a specified time (e.g., 1 hr) at a specified temperature (e.g., 37° C.) in a specified buffer. The total units in a particular cocktail are defined as the sum of the units of the individual component endonucleases of the cocktail. Accordingly, since the starting amount of DNA is known, together with the number of units of endonuclease which are to be used, the appropriate digestion time can be calculated. For example if 18 ng of DNA is to be digested using 56 units of an endonuclease cocktail, the digestion would have to proceed for at least 72 hours in order to achieve complete digestion within the meaning of the present invention. In another example, where 5 ng of DNA is sought to be digested with an enzyme cocktail of 110 units, a digestion time of at least 8 hours would be used.

The subject digestion can be performed at any suitable temperature, such as at 37° C. As would be understood by the skilled person, different restriction enzymes may function optimally at different temperatures. The optimal temperature at which to use a given enzyme is well known in the art.

It should be understood that in addition to digesting the DNA with the subject methylation specific restriction endonucleases, one may also include additional reagents as may be deemed useful. For example, one may also elect to use reagents which further assist in driving digestion, such as recognition site-containing oligonucleotide duplexes, self-complementary oligonucleotides or an oligonucleotide stimulator such as 5-TATAGCCGGCTATA (SEQ ID NO: 1). These mechanisms of assisting with driving digestion are well known to those of skill in the art. In one embodiment, where HpaII is used, there is also introduced into the digestion a HpaII oligonucleotide stimulator. In another example, one may also use an exonuclease which digests single stranded DNA, such as 0.15U exonuclease I per hour. Still further, one may include suitable internal controls, such as a control which confirms that complete digestion has been achieved.

As detailed hereinbefore, one of the major advances of this method is the fact that complete digestion of the DNA sample can be routinely and reliably obtained. Prior art methods have, to date, been limited by the fact that complete digestion of a DNA sample has not been reliably achievable. For this reason, all prior art methods have required that one divides a test DNA sample into two aliquots wherein one aliquot is digested and the corresponding sample is not. Both samples are then amplified and the amplification results are expressed as a ratio of the digested sample amplification results to the non-digested sample amplification results. Accordingly, these results have been relative in nature. The prior art methods did not enable absolute quantitation. It should be understood that this prior art undigested control sample is referred to in step (iv) of the present method as a "corresponding undigested sample". This sample is therefore undigested, but nevertheless, amplified using the same primers and amplification conditions as specified in step (iii) for the digested sample. It should also be understood that this sample is also referred to in the literature as an "undigested internal reference sample".

Reference to "contacting" a sample with a methylation specific restriction endonuclease should be understood as a reference to facilitating the mixing of the methylation specific restriction endonucleases with the DNA sample such that interaction, and therefore digestion, can occur. Means of achieving this objective would be well known to those of skill in the art.

The digested DNA sample of the present invention is quantitatively amplified using primers which flank the methylation specific restriction endonuclease recognition sequence region. As detailed hereinbefore, this "region" may be selected to encompass the full or a substantial part of the length of the gene, in which case the amplicons which are generated will be quite long. Alternatively, the region may correspond to a much shorter stretch of the gene where one or more recognition sequences are clustered. In this case the amplicons which are generated would be significantly shorter.

It should be appreciated that in performing the amplification step, this can be achieved using any one of a number of suitable techniques. For example, where more than one pair of forward/reverse primers are used, directed to targeting two or more separate recognition sequence regions, one may introduce all these primers to a single sample and amplify the sample using a multiplexed amplification technique. Alternatively, one may elect to divide the digested sample of step (ii) into more than one aliquot wherein each aliquot is amplified using a separate pair of primers. It should also be understood that the skilled person may elect to adapt this method so as to use multiple sets of primers, directed to amplifying only one methylation specific restriction endonuclease recognition sequence region but where the multiple primers reflect the application of a nested PCR reaction.

Reference to a "primer" should be understood as a reference to any molecule comprising a sequence of nucleotides, or functional derivatives or analogues thereof, the function of which includes both hybridisation to a DNA sequence which flanks the methylation specific restriction endonuclease recognition sequence region and amplification of the DNA sequence 5' to that region. It should be understood that the primer may comprise non-nucleic acid components. For example, the primer may also comprise a non-nucleic acid tag such as a fluorescent or enzymatic tag or some other non-nucleic acid component which facilitates the use of the molecule as a probe or which otherwise facilitates its detection. In another example, the primer may be a protein nucleic acid which comprises a peptide backbone exhibiting nucleic acid side chains. Preferably, said primer is a single stranded DNA oligonucleotide.

Reference to "forward primer" should be understood as a reference to a primer which amplifies the target DNA in the DNA sample of interest by hybridising to the antisense strand of the target DNA.

Reference to "reverse primer" should be understood as a reference to a primer which amplifies the target DNA in the DNA sample of interest and in the PCR by hybridising to the sense strand of the target DNA.

The design and synthesis of primers suitable for use in the present invention would be well known to those of skill in the art. In one embodiment, the subject primer is 4 to 60 nucleotides in length, in another embodiment 10 to 50 nucleotides in length, in yet another embodiment 15 to 45 nucleotides in length, and in still another embodiment 20 to 40 nucleotides in length.

In terms of the number of primers which are used in the method of the invention, this can be determined by the person of skill in the art. With regard to the total number of primers, the variables which require consideration are the size and number of DNA regions which are being amplified and the distance between the sequences to which the primers hybridise. In order to amplify PCR fragments which are larger than about 1 kb, the primers can be designed to function in a nested PCR method and to hybridise at intervals of approximately 500 bases.

As detailed hereinbefore, where multiple DNA regions are to be amplified, the skilled person may design multiplexed amplification reactions. Alternatively, several individual amplification reactions which each use one unique primer pair may be performed. These methods become relevant where one is amplifying two or more separate methylation specific restriction endonuclease recognition sequence regions or where the methylation of more than one gene is to be analysed. In this case, subsequently to digestion of the sample with the methylation specific restriction endonucleases, one may divide the sample into two aliquots, if two genes are sought to be analysed (such as BCAT1 and IKZF1) with each aliquot then being amplified using the one or more sets of forward and reverse primers directed to the relevant methylation specific restriction endonuclease recognition sequence regions of that gene. Alternatively, a multiplexed reaction can be performed on a single sample wherein the reaction is multiplexed in terms of the use of primers directed to the selected methylation specific restriction endonuclease recognition sequence region of one gene and the use of another set of primers directed to the selected methylation specific restriction endonuclease recognition sequence region of the other gene. As would be familiar to the skilled person, multiplexed reactions can be designed to be performed with two, three or more sets of primers in the context of two or more methylation specific restriction endonuclease recognition sequence regions and/or two or more genes. It should be understood that it would be well within the skill of the person in the art to appropriately design multiplexed or nested amplification reactions.

In one embodiment, to the extent that the method of the present invention is directed to screening for methylated GRASP using HhaI/HpaII digestion, the amplification step is performed using:

(i)
Forward primer:
(SEQ ID NO: 2)
5'-CAAGTTGAAGGTCCGAGAGC;
and (ii)
Reverse primer:
(SEQ ID NO: 3)
5'-CGCACTTCCTCAGAGTGAGA.

In another embodiment, to the extent that the method of the present invention is directed to screening for methylated BCAT1 using HhaI/HpaII digestion, the amplification step is performed using:

(i)
Forward primer:
(SEQ ID NO: 4)
5'-AGATCCCAAGGGTCGTAGC;
and (ii)
Reverse primer:
(SEQ ID NO: 5)
5'-ACTGCCCCAGGTCTTGCT.

In still another embodiment, to the extent that the method of the present invention is directed to screening for methylated IKZF1 using HhaI/HpaII digestion, the amplification step is performed using:

(i)
Forward primer:
(SEQ ID NO: 6)
5'-GGAGTTGCGGCTGAGAC;
and (ii)
Reverse primer:
(SEQ ID NO: 7)
5'-AGAGCGGGACACGGAGA.

Reference to "quantitatively amplifying" the digested DNA should be understood as a reference to performing any suitable quantitative DNA amplification method. This includes, for example, quantitative PCR or quantitative linear amplification. In one embodiment there is used real-time quantitative forms of PCR, such as, for example, TaqMan (Holland et al., *Proc. Natl. Acad. Sci. USA*, 88:7276-7280, 1991; Lee et al., *Nucleic Acid Res.* 21:3761-3766, 1993), Beacon or Scorpion. Methods of quantitative amplification are disclosed in, e.g., U.S. Pat. Nos. 6,180,349; 6,033,854; and 5,972,602, as well as in, e.g., Gibson et al., *Genome Research* 6:995-1001 (1996); DeGraves, et al., *Biotechniques* 34(1):106-10, 112-5 (2003); Deiman B, et al., *Mol. Biotechnol.* 20(2):163-79 (2002). These methods are well known to the person of skill in the art. Without limiting this embodiment to any one theory or mode of action, qPCR is performed in the presence of three oligonucleotides, a forward and reverse primer that flank the region sought to be amplified and a probe that hybridizes between the two primers. It can also be performed in the presence of two oligonucleotides and a fluorescent intercalating dye, such has sybr green. In the context of the former method, the probe is dual labelled with a 5' fluorescent reporter and a 3' quencher (or vice versa). When the probe is intact, the quencher dye absorbs the fluorescence of the reporter due to their proximity. Following annealing to the PCR product the probe is cleaved by 5' to 3' exonuclease activity of, for example, Taq DNA polymerase. This cleavage releases the reporter from the quencher thereby resulting in an increased fluorescence signal that can be used to estimate the initial template methylation level. Alternatively, rather than using a labelled probe that requires cleavage, a probe, such as, for example, a Molecular Beacon is used (see, for example, Mhlanga and Malmberg, *Methods* 25:463-471, 2001). Molecular beacons are single stranded nucleic acid molecules with a stem-and-loop structure. The loop structure is complementary to a region between the primers. The stem structure is formed by annealing two "arms" complementary to each other, which are on either side of the probe (loop). A fluorescent moiety is bound to one arm and a quenching moiety that suppresses any detectable fluorescence when the molecular beacon is not bound to a target sequence is bound to the other arm. Upon binding of the loop region to its target nucleic acid the arms are separated and fluorescence is detectable.

As detailed hereinbefore, one of the significant advantages of the present method is that it enables absolute quantification using methods such as cycle threshold value from a real time PCR instrument where the presence of any signal indicates the presence of methylated DNA. This can be accomplished by comparison to a standard curve run in the same qPCR conditions, containing known quantities of either non-restriction endonuclease-digested wild-type DNA, or restriction-endonuclease-digested, fully methylated DNA. Accordingly, the performance of internal controls in order to compensate for incomplete digestion is not needed and the readout which is obtained by the method of the invention therefore provides an absolute value rather than a relative ratio. Nevertheless, it should be understood that the quantitative readout which is obtained by the present method may be sought to be compared to a quantitative result from a normal individual or from an earlier sample obtained from the patient in issue. This would allow tracking of changes to DNA methylation levels.

Facilitating the interaction of the primer with the target DNA may be performed by any suitable method. Those methods will be known to those skilled in the art. To this end, it should be understood that the primers can be incorporated into the reaction tube at any suitable time point. While incorporation is generally prior to the commencement of the initial amplification cycles, incorporation of one or more additional primers may be performed subsequently to the initial amplification cycles. The mode of incorporation of the primers will depend on how the skilled person is seeking to perform the amplification reaction but, in general, for ease of use and avoidance of contamination, it is usually desirable to be able to perform the entire reaction in a single tube. Nevertheless, any other method of achieving the steps of the invention can be used.

Although the preferred application of this method is to assess methylation levels for the purpose of diagnosing disease onset (such as neoplasia development or predisposition thereto), the detection of converse changes in the levels of said methylation may be desired under certain circumstances, for example, to monitor the effectiveness of therapeutic or prophylactic treatment directed to modulating a neoplastic condition, such as adenoma or adenocarcinoma development. For example, where elevated levels of methylation indicate that an individual has developed a condition characterised by adenoma or adenocarcinoma development, screening for a decrease in the levels of methylation subsequently to the onset of a therapeutic treatment regime may be utilised to indicate successful clearance of the neoplastic cells. In another example, one can use this method to test the tissue at the margins of a tumour resection in order to determine whether the full margin of the tumour has been removed.

The present method can therefore be used in the diagnosis, prognosis, classification, prediction of disease risk, detection of recurrence of disease, selection of treatment of a number of types of neoplasias and monitoring of neoplasias. A cancer at any stage of progression can be detected, such as primary, metastatic, and recurrent cancers. Still further, this method has applications in any other context where analysis of DNA methylation is necessitated.

Using neoplasia development as a non-limiting example, the present invention provides methods for determining whether a mammal (e.g., a human) has a neoplasia, whether a biological sample taken from a mammal contains neoplastic cells or DNA derived from neoplastic cells, estimating the risk or likelihood of a mammal developing a neoplasm, monitoring the efficacy of anti-cancer treatment, or selecting the appropriate anti-cancer treatment in a mammal with cancer. Such methods are based on the determination that many neoplastic cells have a different methylation status than normal cells. Accordingly, by determining whether or not a cell contains differentially methylated sequences it is possible to determine that a cell is neoplastic.

The method of the invention can be used to evaluate individuals known or suspected to have a neoplasia or as a routine clinical test, i.e., in an individual not necessarily suspected to have a neoplasia. Further diagnostic assays can be performed to confirm the status of neoplasia in the individual.

Further, the present methods may be used to assess the efficacy of a course of treatment. For example, the efficacy of an anti-cancer treatment can be assessed by monitoring DNA methylation over time in a mammal having cancer. For example, a reduction or absence of methylation in any of the relevant diagnostic sequences in a biological sample taken from a mammal following a treatment, compared to a level in a sample taken from the mammal before, or earlier in, the treatment, indicates efficacious treatment.

The method of the present invention is therefore useful as a one-time test or as an on-going monitor of those individuals thought to be at risk of disease development or as a monitor of the effectiveness of therapeutic or prophylactic treatment regimes. In these situations, mapping the modulation of methylation levels in any one or more classes of biological samples is a valuable indicator of the status of an individual or the effectiveness of a therapeutic or prophylactic regime which is currently in use. Accordingly, the method of the present invention should be understood to extend to monitoring for increases or decreases in methylation levels in an individual relative to their normal level, or relative to one or more earlier methylation levels determined from a biological sample of said individual.

The present invention is further described by reference to the following non-limiting examples.

EXAMPLE 1

Digestion with Restriction Enzymes to Assay Methylation Status in BCAT1 and GRASP gene loci The protocol includes reagents and methods to extract free circulating DNA from blood plasma and digest free circulating-DNA with the methylation sensitive enzymes HhaI, HpaII and Exonuclease I. The level of BCAT1 and GRASP methylation is then determined.

1. QIAGEN 'isolation of circulating nucleic acids in sera/plasma':

| | | |
|---|---|---|
| a. | QIAGEN ® Mini columns | 50 |
| b. | Tube Extenders (20 ml) | 2 × 25 |
| c. | VacConnectors | 50 |
| d. | Buffer ACL | 2 × 85 mL |
| e. | Buffer ACB | 2 × 190 mL |
| f. | Buffer ACW1 | 2 × 20 mL |
| g. | Buffer ACW2 | 2 × 25 mL |
| h. | Buffer Extraction Ethanol | 2 × 25 mL |
| i. | Buffer AVE (purple caps) | 4 × 1984 L |
| j. | QIAGEN Proteinase K | 4 × 7 mL |
| k. | Carrier RNA (1 g/L) | 2 × 160 L |

2. Control Plasma Specimens

| | | |
|---|---|---|
| a. | POSCONT: spiked with 5 ng fully methylated DNA | 2 × 4 mL |
| b. | NEGCONT: pool plasma from >8 non-disease patients | 2 × 4 mL |

Required Equipment

| Equipment | Quantity | Description | Notes |
|---|---|---|---|
| QIAcube | 2 | Qiagen Cat No. 9001293 | Each Qiacube can process 12 samples at one time, running the manufacturer's protocol Cleanup_QIAampCirculatingNA_SerumOrPlasma_Standard_V1 with elution volume set to 40 uL |
| Thermocycler | 1 | Heated Lid<br>96 well block<br>Accuracy = ±0.5° C.<br>Uniformity = ±0.5° C.<br>Heating = 3° C.<br>Cooling = 2° C. | For example Axygen Maxygene Cat No. THERM-1000 |
| Biosafety Cabinet | 1 | Equipped with HEPA filter and UV sterilisation lamps | n/a |
| Centrifuge | 1 | Supports 1.5 mL microcentrifuge tubes at a max speed of 20,000 g<br>Supports 96 well plates at a max speed of 500 g | For example Eppendorf 5804R Cat No. 5805 000.017<br>For example Labnet MPS 1000 from Sigma Aldrich Cat No. Z723533-1EA |
| Pipette | 1 | Pipette 0.5 L-10 L | n/a |
| | 1 | Pipette 10 L-100 L | n/a |
| | 1 | Pipette 20 L-200 L | n/a |
| | 1 | Pipette 100 L-1000 L | n/a |
| | 1 | Pipette 500 L-5000 L | n/a |
| | 1 | 8-channel Pipette 10 L-100 L | n/a |
| | 1 | Pipette aid | n/a |
| QIAvac 24 plus with Vacuum Pump + accessories | 1 | Qiagen Qiavac 24 plus Cat No. 19413<br>Qiagen Vacuum Pump Cat No. 84000 or | n/a<br>n/a |
| | 1 | 84010 or 84020 | |
| Water bath | 1 | Capable of achieving 60° C. with a calibrated temperature monitor | If the unit does not have a temperature monitor a calibrated thermometer is suitable |
| Vortex | 1 | Capable of 3000 rpm | n/a |
| Ice Machine | 1 | n/a | n/a |
| Laboratory timer | 1 | n/a | n/a |
| Refrigerator | 1 | Capable of 2°-8° Celsius | n/a |
| Freezer | 1 | Capable of -70° Celsius | n/a |

DNA Extraction

The procedure described here is recommended for processing a 24 specimen batch including 22 specimens (4.0 mL 2-spin plasma) plus a negative and positive control ("POSCONT" and "NEGCONT"). The resulting wild type DNA is sufficient for QC analysis (if required) and subsequent restriction-digest assays.

Extraction Procedure

⚠ DNA extraction steps are time sensitive. For maximum DNA yield, the time from specimen thawed (step 2) until initiation of lysis incubation (step 7) should not exceed one hour.

Setup
4. Don a fresh disposable lab coat. Dispose the lab coat at the end of the day.
6. Don a pair of gloves and ensure the gloves extend over the cuffs of the lab coat. Fresh gloves should be used whenever any contamination is suspected; and after each incubation and before handling clean components (e.g. columns, eppendorf tubes, 96-well plates)
7. When working outside of the biosafety cabinet with open containers, don a hair net.
8. Preheat water bath to 60° C.
9. Thaw one tube of positive plasma control, one tube of negative plasma control and 22 specimens at room temperature for 30-60 minutes in a biohazard hood. Ensure that specimens are adequately spaced in hood to allow complete thawing.
10. While the plasma is thawing:
    a. Place a vial of carrier RNA (1 g/L) at room temperature. Once thawed, vortex for 5 seconds and spin in a bench top micro-centrifuge for 5 seconds.
    b. Add 148 L of thawed carrier RNA (1 g/L) to the ACL Buffer (85 mL) and mix by inverting 10 times.
    c. Label 24×50 mL tubes (lid and side) with corresponding unique numbers specific for each specimen for extraction (e.g. 1-24).

Enzyme Digestion
11. Once the specimens are thawed, begin the extraction for each specimen by transferring the plasma to a pre-labelled 50 mL tube for reagent addition. The following components (including specimen) should be added in order for ALL tubes before proceeding to the next component. Use a new tip for each step:
    a. 4 mL plasma, to all tubes then:
    b. 400 L of QIAGEN Proteinase K, to all tubes and swirl, then finally:
    c. 3.2 mL of Buffer ACL (containing carrier RNA) to all tubes.

12. Close the lid of the first 50 mL tube and invert the tube once. Repeat for the remaining 23 tubes.
13. Mix thoroughly by vortexing each tube for exactly 30 sec. (Vortexing must be carried out in groups of two tubes.)
14. Incubate the plasma-extraction solutions in the 60° C. water bath for 30 min.
15. Prepare the QIAvac 24 plus manifold in a biosafety cabinet as described by the manufacturer Lysis
16. Remove the 50 mL tubes from the waterbath.
17. Spin each of the 50 mL tubes in a centrifuge for 10 seconds to ensure all the lysate is at the bottom of the tube.
18. Place tubes in a biosafety cabinet and add 7.2 mL of Buffer ACB to each tube using a new tip for each specimen.
19. Close the cap of the first tube and invert once. Repeat for the remaining 23 tubes. Mix thoroughly by pulse-vortexing for 20 seconds each. Incubate the lysate-Buffer ACB mixture on ice for 5 minutes. (Procedure must be carried out in groups of two tubes at a time.)

Column Purification
20. Carefully decant the lysate-Buffer ACB mixture into the tube extender of the corresponding numbered QIAamp Mini column.
21. Start the vacuum pump (Pump pressure must reach −1000 mbar).
22. During specimen filtering prepare two QIAcubes for DNA extraction as described by the manufacturer QIAcube Extraction
23. Once the specimens are completely drawn through the columns switch off the vacuum pump and release the pressure to 0 mbar. Carefully remove and discard the tube extender.
24. Place the mini spin columns into the rotor adapters prepared previously. Distribute the 24 samples equally between each of the two QIAcubes (12 specimens each).
25. Open lids of reagent bottles in the QIAcubes and ensure all components are in the correct position.
26. Run the QIAcube as specified by the manufacturer. Ensure the QIAcube completes the pre-run check.
27. Clean QIAvac manifold as described by the manufacturer Manual SECOND Elution for Increased Yield
28. After run completion, remove the rotor adapters from the QIAcube and place them into a QIAcube rack. Transfer the elution tube-column assembly into a suitable rack.
29. For each sample, re-apply the eluate (~37 L) to the centre of the membrane.
30. Close the column lid and incubate at room temperature for 3 minutes.
31. Centrifuge the sample tubes at 20,000 g for 1 min at room temperature to elute the wt-DNA.
32. Discard the columns and transfer 36 L of each wt-DNA sample into a 96-well PCR plate.

Methylation Sensitive Digestion
Digestion Method
DNA Concentration Determination
35. Add 10 L of nuclease free water to 24 wells of a 96-well PCR plate
36. Transfer 2.5 L of each of the 24 extracted DNA samples to a well containing 10 uL nuclease free water
37. Place strip caps on each of the wells
38. Test 2×5 µL of the ⅕ dilution prepared in step 36 in the CFF1 assay described below. Included a 4-fold serial dilution standard curve of fully methylated DNA (Millipore) to enable quantifying the concentration of extracted wildtype DNA, CFF1 Assay:

```
CFF1 FWD Primer:
                                    (SEQ ID NO: 8)
TAA GAG TAA TAA TGG ATG GAT GAT G CFF1 REV Primer
                                    (SEQ ID NO: 9)
CCT CCC ATC TCC CTT CC CFF1 Probe [HEX]
                                    (SEQ ID NO: 10)
ATG GAT GAA GAA AGA AAG GAT GAG T [BHQ1]
```

15 µl reaction containing a final concentration of 630 nM Primers, 200 nM Probe and 3 mM MgCl2 in 1× Platinum Taq buffer.

PCR cycling conditions: 1x Cycle 95° C. for 2 min, followed by 50× cycles of 95° C. for 10 sec, 60° C. for 50 sec 39. Use the CFF1 data to calculate the concentration per µl of the original plasma DNA.
40. Dilute each of the 22 clinical DNA samples, POSCONT and NEGCONT to 0.36 ng/µL (25 µL of each sample required)

Enzymatic Digestion of Extracted DNA
41. FOR EACH GENE LOCUS (i.e GRASP or BCAT1): Prepare a Digestion Mastermix using the following volumes (enough for 22 samples, POSCONT, NEGCONT, 7 Standards and a Blank Control:

| Digestion Mastermix Component | Number of reactions Volume (µL) | 72 Total Volume (µ,L) |
|---|---|---|
| HpaII | 2.66 | 191.52 |
| HhaI | 1.33 | 95.76 |
| ExoI | 0.5 | 36 |
| NEB Buffer 4 | 4.5 | 324 |
| 10x BSA | 4.5 | 324 |
| HpaII oligo stimulator (1048/5uM) 5'-TATAGCCGGCTATA (SEQ ID NO: 1) | 1 | 72 |
| H2O | 20.5 | 1476 |
| Input DNA | 10 | |

DO NOT VORTEX ENZYMES: Mix all reagents thoroughly prior to use

42. Pipette 35 µl of the Digestion Mastermix prepared in step 41 into 32 wells of a 96-well PCR plate as indicated below:

| Digestion Plate | 1 | 2 | 3 | 4 | 5 | 6 | 7 | 8 | 9 | 10 | 11 | 12 |
|---|---|---|---|---|---|---|---|---|---|---|---|---|
| A | 1 | | 9 | | 17 | | 2500 pg CpG | | | | | |
| B | 2 | | 10 | | 18 | | 1250 pg CpG | | | | | |

-continued

| Digestion Plate | 1 | 2 | 3 | 4 | 5 | 6 | 7 | 8 | 9 | 10 | 11 | 12 |
|---|---|---|---|---|---|---|---|---|---|---|---|---|
| C | 3 | | 11 | | 19 | | | | | | 625 pg CpG | |
| D | 4 | | 12 | | 20 | | | | | | 312.5 pg | |
| E | 5 | | 13 | | 21 | | | | | | 156.25 pg | |
| F | 6 | | 14 | | 22 | | | | | | 78.125 pg | |
| G | 7 | | 15 | | BioRec +ve | | | | | | 39.06 pg | |
| H | 8 | | 16 | | BioRec −ve | | | | | | Water | |

43. Add 10 μl of the diluted DNA samples prepared in Step 40 to the appropriate wells and prepare a CpG DNA standard starting at 2500 pg and add to column 7 as above (add 10 μl of water for blank).
44. Seal the plate using BioRad sealing Film and spin down briefly.
45. Mix plate on mixmate for 5 minute at 1200 RPM, spin briefly and mix again on mixmate for a further 5 minutes at 1200 RPM
46. Spin briefly and transfer plate to Axygen Thermocycler. Incubate @ 37° C. for 72 hrs with heated lid at 60° C. (45 μl volume setting)

Detection of Methylated DNA
PCR Setup and Data Interpretation
47. 1 Hour before digestion is scheduled to finish prepare a PCR Mastermix as follows (enough for 70 wells):
BCAT1:

| ASSAY | | | | BCAT1 HpaII_HhaI | | PCR ID |
|---|---|---|---|---|---|---|
| PCR Total Volume | 80 uL | | | | # wells | |
| Template input | 20 uL | | | | 70 | |

| Component | Stock conc. | Supplier | Lot number | Final conc. | uL per well | PCR Mastermix Cocktail - uL required |
|---|---|---|---|---|---|---|
| 10x buffer-MgCl2 | 10X | Invitrogen | | 1X | 8.000 | 560 |
| MgCl2 | 50 mM | Invitrogen | | 3 mM | 4.800 | 336 |
| dNTP mix | 10 mM | Promega | | 200 uM | 1.600 | 112 |
| FWD #1073 | 50 uM | SIGMA | | 328 nM | 0.526 | 36.82 |
| REV #1074 | 50 uM | SIGMA | | 265 nM | 0.427 | 29.89 |
| Probe #1077 | 10 uM | SIGMA | | 100 nm | 0.800 | 56 |
| Platinum Taq DNA polymerase | 5 U/uL | Invitrogen | | 0.033 U/uL | 1.000 | 70 |
| Restriction digest | | | | | 20.000 | — |
| Nuclease-tree water | NA | Promega | | NA | 42.520 | 2976.4 |

| PCR conditions: | | | | |
|---|---|---|---|---|
| 1 cycle | 95 | ° C. | 2 | min |
| 55 cycles | 95 | ° C. | 30 | sec |
| | 60 | ° C. | 30 | sec |
| with acquisition | 72 | ° C. | 45 | sec |
| 1 cycle | 40° C. | ° C. | 10 sec | sec |

Grasp

| ASSAY | | | | GRASP HpaII_HhaI | | PCR ID |
|---|---|---|---|---|---|---|
| PCR Total Volume | 80 uL | | | | # wells | |
| Template input | 20 uL | | | | 34 | |

| Component | Stock conc. | Supplier | Lot number | Final conc. | uL per well | PCR Mastermix Cocktail - uL required |
|---|---|---|---|---|---|---|
| 10x buffer-MgCl2 | 10X | Invitrogen | | 1X | 8.000 | 272 |
| MgCl2 | 50 mM | Invitrogen | | 3 mM | 4.800 | 183.2 |
| dNTP mix | 10 mM | Promega | | 200 uM | 1.600 | 54.4 |
| FWD #1067 | 50 uM | SIGMA | | 280 nM | 0.450 | 15.3 |
| REV #1068 | 50 uM | SIGMA | | 364 nM | 0.580 | 19.72 |
| Probe #1078 | 10 uM | SIGMA | | 100 nm | 0.800 | 27.20 |
| Platinum Taq DNA polymerase | 5 U/uL | Invitrogen | | 0.033 U/uL | 1.000 | 34 |
| Restriction digest | | | | | 20.000 | — |
| Nuclease-free water | NA | Promega | | NA | 42.520 | 1446.68 |

| PCR conditions: | | | | |
|---|---|---|---|---|
| 1 cycle | 95 | ° C. | 2 | min |
| 55 cycles | 95 | ° C. | 15 | sec |
| | 60 | ° C. | 30 | sec |

| | | | | |
|---|---|---|---|---|
| with acquisition | 72 | ° C. | 45 | sec |
| 1 cycle | 40° C. | ° C. | 10 sec | sec |

48. Transfer PCR Mastermix into an 8 well strip and pipette 60 µl of mastermix into columns 1-8 of a 96 well LC480 plate.
49. Once digestion has run for 72 hrs, turn the heated lid on the AXYGEN cycler back to 110° C. and run the plate for 10 minutes at 98° C. to inactivate the HpaII/HhaII and ExoI
50. Remove the plate from the machine and spin briefly to bring all the liquid to the bottom of the well.
51. Carefully remove the sealing film and using a 100 µl multichannel transfer 20 µl (in duplicate) of the digestion reaction into the appropriate well of the qPCR plate (see below)

| qPCR Plate | 1 | 2 | 3 | 4 | 5 | 6 | 7 | 8 |
|---|---|---|---|---|---|---|---|---|
| A | 1 | 1 | 9 | 9 | 17 | 17 | 2500 pg CpG | 2500 pg CpG |
| B | 2 | 2 | 10 | 10 | 18 | 18 | 1250 pg CpG | 1250 pg CpG |
| C | 3 | 3 | 11 | 11 | 19 | 19 | 625 pg CpG | 625 pg CpG |
| D | 4 | 4 | 12 | 12 | 20 | 20 | 312.5 pg | 312.5 pg |
| E | 5 | 5 | 13 | 13 | 21 | 21 | 156.25 pg | 156.25 pg |
| F | 6 | 6 | 14 | 14 | 22 | 22 | 78.125 pg | 78.125 pg |
| G | 7 | 7 | 15 | 15 | BioRec +ve | BioRec +ve | 39.06 pg | 39.06 pg |
| H | 8 | 8 | 16 | 16 | BioRec −ve | BioRec −ve | Water Blank | Water Blank |

52. Seal the plate with LC480 sealing film, spin briefly and mix on mixmate for 30 secs at 1100 RPM. Spin again to gather liquid at bottom of wells.
53. Transfer the plate to an LC480 and run using the following settings: 95° C. for 2 mins followed by 55× Cycles of 95° C. 15 secs, 60° C. 30 secs and 72° C. for 45 secs (Acquisition in FAM Channel).
54. Export Ct values and concentrations for each well for analysis.

TABLE 1

Primers/Probes

| Oligo ID | Gene | Oligo Name | Sequence (5'-3') |
|---|---|---|---|
| 1007 | GRASP | GRASPHhaIHpaIIAMP2 FWD | CAAGTTGAAGGTCCGA GAGC (SEQ ID NO: 2) |
| 1008 | GRASP | GRASPHhaIHpaIIAMP2 REV | CGCACTTCCTCAGAGT GAGA (SEQ ID NO: 3) |
| 1078 | GRASP | GRASPHhaIHpaIIAMP2 PROBE | (FAM) CCGGTGGGAGA AGCGGGCC (TAMRA) (SEQ ID NO: 11) |
| 1073 | BCAT1 | BCAT1 ResEnzym FWD | AGATCCCAAGGGTCGT AGC (SEQ ID NO: 4) |
| 1074 | BCAT1 | BCAT1 ResEnzym REV | ACTGCCCCAGGTCTTG CT (SEQ ID NO: 5) |
| 1077 | BCAT1 | BCAT1 ResEnzym Probe | (FAM) TGCAGAGCGCG GTCCCGG (TAMRA) (SEQ ID NO: 12) |

EXAMPLE 2

IKZF1 DREAMS Assay

DNA was extracted and quantified to enable generation of 25 µL of 0.36 ng/µL wildtype DNA as described in Example 1. A total of 10 µL (3.6 ng DNA) was digested in a total digestion volume of 45 µL as described in Example 1. The methylation status in the IKZF1 gene locus was analysed in an 80 µL PCR reaction with an input of 20 µL digested DNA as described below:

| Oligo ID | Gene | Oligo Name | Sequence 5'-3' |
|---|---|---|---|
| 1082 | IKZF1 | IKZF1 Dreams1 Fwd | GGAGTTGCGGCTGAGAC (SEQ ID NO: 6) |
| 1083 | IKZF1 | IKZF1 Dreams1 Rev | AGAGCGGGACACGGAGA (SEQ ID NO: 7) |
| 1119 | IKZF1 | IKZF1 Dreams1 Probe | (HEX) TTCTGCGCGCCC CGCTCC (BHQ1) (SEQ ID NO: 13) |

Assay:
1× Liberty Taq mastermix (Life Technologies), 3 mM MgCl2 (final), 200 nM Fwd primer, 200 nM Rev primer, 100 nM probe.
PCR Cycling:

| | | | | |
|---|---|---|---|---|
| 1 cycle | 95 | ° C. | 2 | min |
| 50 cycles | 95 | ° C. | 10 | sec |
| with acquisition (HEX) | 63 | ° C. | 40 | sec |
| 1 cycle | 40 | ° C. | 10 sec | sec |

EXAMPLE 3

IKZF1/BCAT1 DREAMS Duplex Assay

DNA was extracted and quantified to enable generation of 25 µL of 0.36 ng/µL wildtype DNA as described in Example 1. A total of 10 µL (3.6 ng DNA) was digested in a total digestion volume of 45 µL as described in Example 1. The methylation status in gene loci, BCAT1 and IKZF1 was analysed simultaneously in an 80 µL PCR reaction with an input of 20 µL digested DNA as described below:

| Oligo ID | Gene | Oligo Name | Sequence 5'-3' |
|---|---|---|---|
| 1082 | IKZF1 | IKZF1 Dreams1 Fwd | GGAGTTGCGGCTGAGAC (SEQ ID NO: 6) |
| 1083 | IKZF1 | IKZF1 Dreams1 Rev | AGAGCGGGACACGGAGA (SEQ ID NO: 7) |
| 1119 | IKZF1 | IKZF1 Dreams1 Probe | (HEX)TTCTGCGCGCCCCGCTCC (BHQ1) (SEQ ID NO: 13) |
| 1073 | BCAT1 | BCAT1 ResEnzym Fwd | AGATCCCAAGGGTCGTAGC (SEQ ID NO: 4) |
| 1074 | BCAT1 | BCAT1 ResEnzym Rev | ACTGCCCCAGGTCTTGCT (SEQ ID NO: 5) |
| 1077 | BCAT | BCAT1 ResEnzym Probe | (FAM)TGCAGAGCGCGGTCCCGG (TAMRA) (SEQ ID NO: 12) |

Assay:
1× Liberty Taq mastermix (Life Technologies), 3 mM MgCl2 (final), 200 nM Fwd primers, 200 nM Rev primers, 100 nM probes.
PCR Cycling:

| 1 cycle | 95 | °C. | 2 | min |
|---|---|---|---|---|
| 50 cycles | 95 | °C. | 10 | sec |
| with acquisition (FAM/HEX) | 63 | °C. | 40 | sec |
| 1 cycle | 40 | °C. | 10 sec | sec |

Those skilled in the art will appreciate that the invention described herein is susceptible to variations and modifications other than those specifically described. It is to be understood that the invention includes all such variations and modifications. The invention also includes all of the steps, features, compositions and compounds referred to or indicated in this specification, individually or collectively, and any and all combinations of any two or more of said steps or features.

BIBLIOGRAPHY

DeGraves, et al., *Biotechniques* 34(1):106-10, 112-5 (2003)
Deiman B, et al., *Mol. Biotechnol.* 20(2):163-79 (2002)
Frommer et al., *Proc. Natl. Acad. Sci. USA*, 89:1827-1831, 1992
Gibson et al., *Genome Research* 6:995-1001 (1996)
Herman et al., *Proc. Natl. Acad. Sci. USA*, 93:9821-9826, 1992
Holland et al., *Proc. Natl. Acad. Sci. USA*, 88:7276-7280, 1991
Lee et al., *Nucleic Acid Res.* 21:3761-3766, 1993
Levenson & Melnikov, *Expert Rev. Molecule. Diagn.* 11(8): 807-812, 2011
Markowitz and Bertagnolli (2009). *N. Engl. J. Med.* 361 (25):2449-60
Sadri and Hornsby, *Nucl. Acids Res.* 24:5058-5059, 1996
Weitzel J N (1999). *Cancer* 86 (11 Suppl): 2483-92
Xiong and Laird, *Nucl. Acids Res.* 25:2532-2534, 1997

The invention claimed is:

1. A method of quantitatively screening for the methylation of a DNA region of interest in a biological sample, said method comprising:
   (i) contacting DNA from said biological sample with two or more methylation-sensitive restriction endonucleases and digesting said DNA at 4-6 pg of said DNA per unit of said endonucleases per hour;
   (ii) quantitatively amplifying the digested DNA sample of step (i) using one or more forward primers and one or more reverse primers, which primers are directed to DNA sequences flanking one or more methylation specific restriction endonuclease recognition sequence regions; and
   (iii) quantifying the level of said methylated DNA region of interest.

2. The method according to claim 1 wherein said quantification does not require determining the ratio of the amplified DNA of step (ii) relative to a corresponding undigested sample.

3. The method according to claim 2 wherein step (ii) is performed in the presence of one or more probes.

4. The method of claim 3 wherein said probe is a hydrolysis probe.

5. The method according to claim 1 wherein said DNA is a gene.

6. The method according to claim 5 wherein said gene is a mammalian gene.

7. The method according to claim 6 wherein said mammalian gene is a large intestine neoplasm marker.

8. The method according to claim 7 wherein said gene is one or more of the gene loci BCAT1, IKZF1, IRF4, GRASP and CAHM.

9. The method according to claim 1 wherein said method comprises:
   (i) extracting the DNA from said biological sample and establishing the concentration of total DNA present in said sample;
   (ii) contacting DNA from said biological sample with two or more methylation-sensitive restriction endonucleases and digesting said DNA at 4-6 pg of said DNA per unit of said endonucleases per hour;
   (iii) quantitatively amplifying the digested DNA sample of step (ii) using one or more forward primers and one or more reverse primers, which primers are directed to DNA sequences flanking one or more methylation specific restriction endonuclease recognition sequences; and
   (iv) quantifying the level of said methylated DNA region of interest wherein said quantification does not require determining the ratio of the amplified DNA of step (iii) relative to a corresponding undigested sample.

10. The method according to claim 9 wherein 1-20 ng of the DNA extracted in step (i) is subjected to the digestion step of (ii).

11. The method according to claim 10 wherein 1-15 ng or 1-10 ng of DNA is used.

12. The method according to claim 11 wherein 2 ng, 3 ng, 4 ng, 5 ng, 6 ng, 7 ng, 8 ng or 9 ng of DNA is used.

13. The method according to claim 1 wherein said two or more methylation specific restriction endonucleases include at least one Type IIe enzyme.

14. The method according to claim 13 wherein said Type IIe enzyme is HpaII.

15. The method according to claim 14 wherein the digestion step is performed using the methylation specific restriction endonucleases HpaII, HhaI and the exonuclease ExoI.

16. The method according to claim 14 wherein said method is directed to screening for methylated GRASP using HhaI/HpaII digestion and the amplification step is performed using:

```
(i)
Forward primer:
                                        (SEQ ID NO: 2)
5'-CAAGTTGAAGGTCCGAGAGC;
and (ii)
Reverse primer:
                                        (SEQ ID NO: 3)
5'-CGCACTTCCTCAGAGTGAGA.
```

17. The method according to claim 14 wherein said method is directed to screening for methylated BCAT1 using HhaI/HpaII digestion and the amplification step is performed using:

```
(i)
Forward primer:
                                        (SEQ ID NO: 4)
5'-AGATCCCAAGGGTCGTAGC;
and (ii)
Reverse primer:
                                        (SEQ ID NO: 5)
5'-ACTGCCCCAGGTCTTGCT.
```

18. The method according to claim 14 wherein said method is directed to screening for methylated IKZF1 using HhaI/HpaII digestion and the amplification step is performed using:

```
(i)
Forward primer:
                                        (SEQ ID NO: 6)
5'-GGAGTTGCGGCTGAGAC;
and (ii)
Reverse primer:
                                        (SEQ ID NO: 7)
5'-AGAGCGGGACACGGAGA.
```

19. The method according to claim 1 wherein said biological sample is a blood sample, biopsy sample or stool sample.

* * * * *

SEQUENCE LISTING

<160> NUMBER OF SEQ ID NOS: 13

<210> SEQ ID NO 1
<211> LENGTH: 14
<212> TYPE: DNA
<213> ORGANISM: Artificial Sequence
<220> FEATURE:
<223> OTHER INFORMATION: Oligonucleotide stimulator

<400> SEQUENCE: 1
tatagccggc tata       14

<210> SEQ ID NO 2
<211> LENGTH: 20
<212> TYPE: DNA
<213> ORGANISM: Artificial Sequence
<220> FEATURE:
<223> OTHER INFORMATION: Primer

<400> SEQUENCE: 2
caagttgaag gtccgagagc       20

<210> SEQ ID NO 3
<211> LENGTH: 20
<212> TYPE: DNA
<213> ORGANISM: Artificial Sequence
<220> FEATURE:
<223> OTHER INFORMATION: Primer

<400> SEQUENCE: 3
cgcacttcct cagagtgaga       20

<210> SEQ ID NO 4
<211> LENGTH: 19
<212> TYPE: DNA
<213> ORGANISM: Artificial Sequence
<220> FEATURE:
<223> OTHER INFORMATION: Primer

<400> SEQUENCE: 4
agatcccaag ggtcgtagc                                              19

<210> SEQ ID NO 5
<211> LENGTH: 18
<212> TYPE: DNA
<213> ORGANISM: Artificial Sequence
<220> FEATURE:
<223> OTHER INFORMATION: Primer

<400> SEQUENCE: 5
actgccccag gtcttgct                                               18

<210> SEQ ID NO 6
<211> LENGTH: 17
<212> TYPE: DNA
<213> ORGANISM: Artificial Sequence
<220> FEATURE:
<223> OTHER INFORMATION: Primer

<400> SEQUENCE: 6
ggagttgcgg ctgagac                                                17

<210> SEQ ID NO 7
<211> LENGTH: 17
<212> TYPE: DNA
<213> ORGANISM: Artificial Sequence
<220> FEATURE:
<223> OTHER INFORMATION: Primer

<400> SEQUENCE: 7
agagcgggac acggaga                                                17

<210> SEQ ID NO 8
<211> LENGTH: 25
<212> TYPE: DNA
<213> ORGANISM: Artificial Sequence
<220> FEATURE:
<223> OTHER INFORMATION: Primer

<400> SEQUENCE: 8
taagagtaat aatggatgga tgatg                                       25

<210> SEQ ID NO 9
<211> LENGTH: 17
<212> TYPE: DNA
<213> ORGANISM: Artificial Sequence
<220> FEATURE:
<223> OTHER INFORMATION: Primer

<400> SEQUENCE: 9
cctcccatct cccttcc                                                17

<210> SEQ ID NO 10
<211> LENGTH: 25
<212> TYPE: DNA
<213> ORGANISM: Artificial Sequence
<220> FEATURE:

```
<223> OTHER INFORMATION: Probe

<400> SEQUENCE: 10
atggatgaag aaagaaagga tgagt                                              25

<210> SEQ ID NO 11
<211> LENGTH: 19
<212> TYPE: DNA
<213> ORGANISM: Artificial Sequence
<220> FEATURE:
<223> OTHER INFORMATION: Probe

<400> SEQUENCE: 11
ccggtgggag aagcgggcc                                                     19

<210> SEQ ID NO 12
<211> LENGTH: 18
<212> TYPE: DNA
<213> ORGANISM: Artificial Sequence
<220> FEATURE:
<223> OTHER INFORMATION: Probe

<400> SEQUENCE: 12
tgcagagcgc ggtcccgg                                                      18

<210> SEQ ID NO 13
<211> LENGTH: 18
<212> TYPE: DNA
<213> ORGANISM: Artificial Sequence
<220> FEATURE:
<223> OTHER INFORMATION: Probe

<400> SEQUENCE: 13
ttctgcgcgc cccgctcc                                                      18
```